US006383479B1

(12) United States Patent
Aschauer et al.

(10) Patent No.: US 6,383,479 B1
(45) Date of Patent: May 7, 2002

(54) NEUTROPHIL-ACTIVATING FACTOR

(75) Inventors: Heinrich Aschauer, Vienna; Ivan James Daldon Lindley, Brunn/Gebirge, both of (AT); Paola Peveri, Berne; Alfred Walz, Koeniz, both of (CH)

(73) Assignees: Novartis AG, Basel (SE); Theodor Kocher Institut, Bern (SE)

( * ) Notice: Subject to any disclaimer, the term of this patent is extended or adjusted under 35 U.S.C. 154(b) by 0 days.

(21) Appl. No.: 08/466,546

(22) Filed: Jun. 6, 1995

Related U.S. Application Data

(63) Continuation of application No. 08/082,116, filed on Jun. 17, 1993, now abandoned, which is a continuation of application No. 08/011,448, filed on Jan. 29, 1993, now abandoned, which is a continuation of application No. 07/951,249, filed on Sep. 25, 1992, now abandoned, which is a continuation of application No. 07/798,306, filed on Nov. 22, 1991, now abandoned, which is a continuation of application No. 07/381,698, filed as application No. PCT/EP88/01025 on Nov. 12, 1988, now abandoned.

(30) Foreign Application Priority Data

Nov. 19, 1987 (GB) ............................................. 8727053
Mar. 3, 1988 (GB) ............................................. 8805070
Oct. 28, 1988 (GB) ............................................. 8825258

(51) Int. Cl.$^7$ ........................ A61K 38/19; C07K 14/52
(52) U.S. Cl. ..................... 424/85.1; 530/324; 530/344; 514/2; 514/885
(58) Field of Search ................................. 530/324, 344, 530/399; 435/69.5, 69.52; 424/85.1, 85.2; 514/2, 12, 21, 885

(56) References Cited

U.S. PATENT DOCUMENTS

| | | | | |
|---|---|---|---|---|
| 5,302,384 A | | 4/1994 | Gimbrone et al. | .......... 424/85.2 |
| 5,306,627 A | | 4/1994 | Yamada et al. | ............ 435/69.5 |
| 5,652,338 A | * | 7/1997 | Matsushima et al. | ....... 530/351 |

FOREIGN PATENT DOCUMENTS

WO  WO89/04325  5/1989

OTHER PUBLICATIONS

Schroder et al. (1988) J. of Immunol. 140, pp 3534–3548.*
Peveri et al. (1988) J. of Exp. Med. 147, pp 1547–1559.*
Lindley et al. (1988) PNAS 85, pp 9199–9203.*
Tanaka et al. FEBS (1988) 236, pp. 467–470.*
Yoshimura et al. PNAS (1987) 84, pp 9233–9237.*
Gregory et al. Biochem. Biophy. Res Comm 151(2) 1988, pp 883–890.*
Matsushima et al. J. Exp. Med. (1988), 167, pp 1883–1893.*
Watz et al. (1991) J. Exp. Med. vol. 174, pp. 1355–1362.*
Baggiolini et al. FASEB J. 2 (4), Abstract No. 541 (1988).
Baggiolini et al., J. Clin. Invest. 84, 1045–1049 (1989).
Beaubien et al., Biochem. J. 271, 797–801 (1980).
Clore et al., J. Biol. Chem. 264, 18907–18911 (1989).
Inoue et al., Jpn. J. Cancer Res. (Gann) 77, 693–702 (1986).
Jose et al., Biochem. J. 278, 493–497 (1991).
Kownatzki et al., Clin. exp. Immunol. 64, 214–222 (1986).
Kownatzki et al., Immunobiol. 177, 352–362 (1988).
Maestrelli et al., Immunology 64, 219–225 (1988).
Matsushima et al., Lymphokine Res. 7, 325 (1988).
Oppenheim et al., Immunology Letters 16, 179–184 (1987).
Peveri et al., Experientia (Basle) 44, A77 (1988).
Schmid et al., J. Immunol. 139, 250–256 (1987).
Schroder, J. Exp. Med. 170, 847–863 (1989).
Schroder et al., J. Immunol. 139, 3474–3483 (1987).
Schroder et al., J. Leukocyte Biol. 42, 595 (1987).
Schroder et al., Biochem. Biophys. Res. Commun. 152, 277–284 (1988).
Schroder et al., J. Exp. Med. 171, 1091–1100 (1990).
Schroder et al., Biochem. Biophys. Res. Commun. 172, 898–904 (1990).
Tate et al., Biochem. 31, 2435–2442 (1992).
Van Damme et al., J. Exp. Med. 167, 1364–1376 (1988).
Walz et al., Biochem. Biophys. Res. Commun. 149, 755–761 (1987).
Walz et al., Lymphokine Res. 7, 326 (1988).
Yoshimura et al., J. Immunol. 139, 788–793 (1987).
Yoshimura et al., Fed. Proc. 46, 735 (1987).
Yoshimura et al., J. Leukocyte Biology 42, 279–327, Abstract No. 103 only (1987).

* cited by examiner

*Primary Examiner*—Prema Mertz
*Assistant Examiner*—Sarada C Prasad
(74) *Attorney, Agent, or Firm*—Melvyn M. Kassenoff

(57) ABSTRACT

Biologically active, pure neutrophil-activating factor (NAF) isolated from human monocytes or after expression of a synthetic NAF gene in *E.coli* and having the following amino acid sequence
Ser-Ala-Lys-Glu-Leu-Arg-Cys-Gln-Cys-Ile-Lys-Thr-Tyr-Ser-Lys-Pro-Phe-His-Pro-Lys-Phe-Ile-Lys-Glu-Leu-Arg-Val-Ile-Glu-Ser-Gly-Pro-His-Cys-Ala-Asn-Thr-Glu-Ile-Ile-Val-Lys-Leu-Ser-Asp-Gly-Arg-Glu-Leu-Cys-Leu-Asp-Pro-Lys-Glu-Asn-Trp-Val-Gln-Arg-Val-Val-Glu-Lys-Phe-Leu-Lys-ArgAla-Glu-Asn-Ser.

12 Claims, 19 Drawing Sheets

FIG 13

Figure 1:
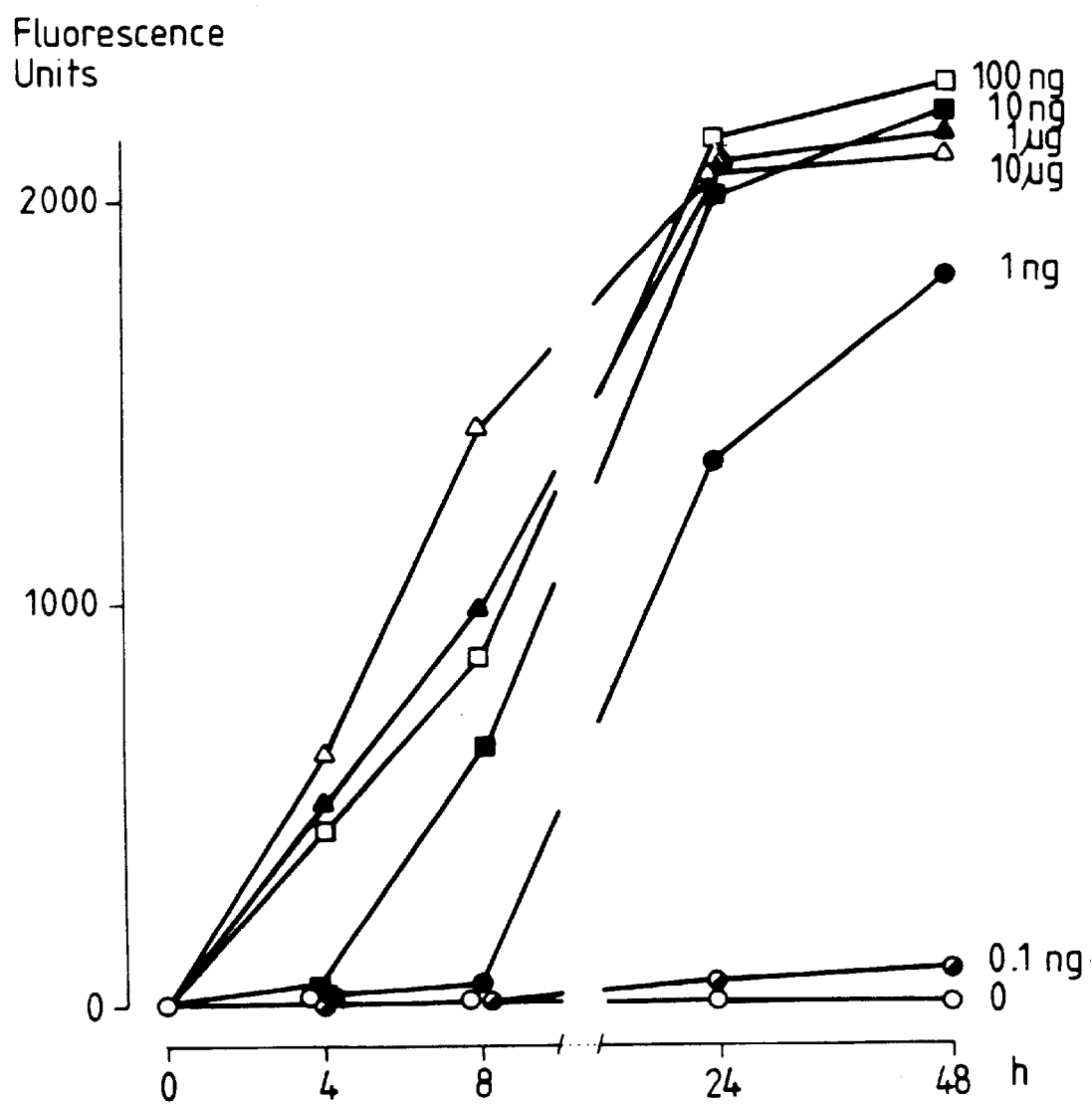

```
   ClaI                              TaqI                                        ·52
<------------------------------------------------ ON-1 -----------------------------
  CATCGATAGCT ATG AGT GCT AAA GAA CTT CGA TGT CAG TGC ATA AAG ACA TAC AGC AAA
GTACGTAGCTATCGA TAC TCA CGA TTT CTT GAA GCT ACA GTC ACG TAT TTC TGT ATG TCG TTT
<------------------------------------------------ ON-2 -----------------------------
            Met Ser Ala Lys Glu Leu Arg Cys Gln Cys Ile Lys Thr Tyr Ser Lys
             1                                   10
                                                                                ·119
-------------------------------->(------------------- ON-3 -----------------
CCT TTC CAC CCC AAA TTT ATC AAA GAA CTG AGA GTG ATT GAG AGT GGA CCA CAC TGC GCC
GGA AAG GTG GGG TTT AAA TAG TTT CTT GAC TCT CAC TAA CTC TCA CCT GGT GTG ACG CGG
-------------------------------->(------------------- ON-4 -----------------
Pro Phe His Pro Lys Phe Ile Lys Glu Leu Arg Val Ile Glu Ser Gly Pro His Cys Ala
                20                                      30
                                                                                ·179
-------------------------------------------------------->(-----------------
AAC ACA GAA ATT ATT GTA AAG CTT TCT GAT GGA AGA GAG CTC TGT CTG GAC CCC AAG GAA
TTG TGT CTT TAA TAA CAT TTC GAA AGA CTA CCT TCT CTC GAG ACA GAC CTG GGG TTC CTT
-------------------------------------------------------->(-----------------
Asn Thr Glu Ile Ile Val Lys Leu Ser Asp Gly Arg Glu Leu Cys Leu Asp Pro Lys Glu
                40                                      50
                                                                       ·230      BamHI
------------------------------------- ON-5 -----------------------------
AAC TGG GTG CAG AGG GTT GTG GAG AAG TTT TTG AAG AGG GCT GAG AAT TCA TAA TAA TGA G
TTG ACC CAC GTC TCC CAA CAC CTC TTC AAA AAC TTC TCC CGA CTC TTA AGT ATT ATT ACT CCTAG
------------------------------------- ON-6 ----------------------------->
Asn Trp Val Gln Arg Val Val Glu Lys Phe Leu Lys Arg Ala Glu Asn Ser  *   *   *
                60                                      70
```

NEUTROPHIL-ACTIVATING FACTOR

This is a continuation of application Ser. No. 08/082,116, filed Jun. 17, 1993 and now abandoned, which is a continuation of application Ser. No. 08/011,448, filed Jan. 29, 1993 and now abandoned, which is a continuation of application Ser. No. 07/951,249, filed Sep. 25, 1992 and now abandoned, which is a continuation of application Ser. No. 07/798,306, filed Nov. 22, 1991 and now abandoned, which is a continuation of application Ser. No. 07/381,698, filed Jul. 31, 1989 and now abandoned, which is a 371 of PCT Application No. PCT/EP88/01025, filed Nov. 12, 1988.

The present invention is concerned with an immunomodulatory substance.

It is more particularly concerned with an immunostimulating factor capable of activating human neutrophil leukocytes, hereinafter designated neutrophil-activating factor (NAF).

1. BACKGROUND

The neutrophil leukocytes (neutrophils) are the most common leukocytes and account for about ⅔ of the white cells in human blood. They have one main function, which is to protect the host organism against microbial infections. The neutrophils are mobile, are responsive to chemotactic stimuli generated upon infection, and are able to move into infected tissues to kill the microorganisms. The killing depends on the ability of the neutrophils to engulf the microorganisms and to release oxygen radicals and microbiocidal enzymes (B. M. Babior, New Engl. J. Med. 298 [1978] 659–668 and M. Baggiolini, Experientia 40 [1984] 906–909). The release of such products depends on activation of the neutrophils. Substances like the neutrophil-activating factor described herein could thus be employed to enhance neutrophil activation and therefore the antimicrobial defense mechanism of the human body.

We have now found that human monocytes secrete a factor that induces exocytosis and the respiratory burst (oxygen radical formation and enzyme release) in human neutrophils and thus displays neutrophil-activating properties which are important in antimicrobial activity.

The factor can be obtained from the culture fluid of stimulated human monocytes and has an apparent molecular weight of approximately 6000, more precisely about 6500, in SDS-gel electrophoresis.

Monocytes are phagocytic cells similar to neutrophils. In contrast to neutrophils, however, monocytes are long-lived. They migrate from the blood into all possible tissue sites where they transform into macrophages. The transformation from monocytes to macrophages can also be observed in cell culture experiments. The macrophages in the tissues have a variety of functions, mainly phagocytosis of unwanted material and production of a great variety of peptides and proteins which are secreted. Macrophages collect at the site of persisting infection and it is at these locations that the production of NAF by these cells could enhance the host-defence capabilities of neutrophils and thus have a pathophysiologically relevant function.

NAF is characterized by its neutrophil-activating properties, i.e. the induction of the so-called respiratory burst with production of oxygen radicals and the induction of enzyme release. In molecular terms NAF, is characterized by the following properties: an apparent molecular weight of about 6500 in SDS-gel electrophoresis, an isoelectric point of approximately 8.6, resistance to heat up to 80° C. and to a number of denaturing agents but susceptibility to proteases, suggesting that NAF is a polypeptide. The action of NAF on human neutrophils is similar to that of two known chemotactic stimuli, the anaphylatoxin C5a and the bacterial peptide N-formyl-L-methionyl-L-leucyl-L-phenylalanine (fMLP), but is mediated by a surface receptor to which NAF binds and which differs from the receptors of any known agonist of human neutrophils. NAF is produced in culture by human monocytes but not by human lymphocytes. Production depends on the presence of a stimulus like bacterial lipopolysaccharide (LPS), phytohaemagglutinin (PHA), or concanavalin A (ConA) and on stimulus concentration and incubation time. It is inhibited by cycloheximide, indicating that de novo synthesis of protein is involved.

As already indicated, monocytes and macrophages are abundant sources of a variety of bioactive peptides and proteins (C. F. Nathan, J. Clin. Invest. 79 [1987] 319–326). They have been identified as the producers of three distinct cytokines: interleukin 1 (IL-l), tumor necrosis factor (TNF) and interferon-alpha (IFN-α). A number of reports have been published showing that monocytes and macrophages also produce factors acting on neutrophils which are different from those mentioned above. Since they are active on neutrophils these factors are presented hereafter in some detail. It was reported in various publications that alveolar macrophages release factors which are chemotactic for neutrophils (J. A. Kazmierowski et al., J. Clin. Invest. 59 [1977] 273–281; W. W. Merrill et al., J. Clin. Invest. 65 [1980] 268–270 and G. W. Hunninghake et al., J. Clin. Invest. 66 [1980] 473–483) and which can enhance the antimicrobial defense in the lung. It was shown subsequently that these factors enhance the microbiocidal activity of neutrophils (J. E. Pennington et al., J. Infect. Dis. 148 [1983] 101–109 and J. Clin. Invest. 75 [1985] 1230–1237). Purification by gel filtration and chromatofocusing led to the identification of a protease-sensitive factor (termed NAF) produced by alveolar macrophages, with a molecular weight of 6000 and an isoelectric point of 7.6. This factor was reported to be weakly chemotactic and to enhance the killing of phagocytosed bacteria by neutrophils without, however, inducing by itself the production of oxygen radicals nor the release of enzymes. A similar mechanism of enhanced anti-microbial activity was described by other workers (A. Ferrante et al., Clin. Exp. Immunol. 56 [1984] 559–566), who showed that human neutrophils required the addition of culture media from monocytes or macrophages to induce the killing of Neigleria fowleri. Granulocyte-activating mediators (GRAM) produced by LPS-simulated human monocytes were described by other laboratories (A. Kapp et al., J. Invest. Dermatol. 86 [1986] 523–528 and F. E. Maly et al., Lymphokine Res. 5 [1986] 21–33). Two GRAM species were described, a major one with an apparent molecular weight of 60,000 and a minor one with an apparent molecular weight of 10,000, which induced a delayed respiratory burst response in human neutrophils, as revealed by chemiluminescence. These factors are sensitive to heat and trypsin and their production is dependent on stimulation of the monocytes with LPS and, apparently, on de novo protein synthesis.

Several reports describe factors derived from monocytes and/or macrophages with chemotactic activity towards neutrophils. A factor termed "mononuclear cell-derived chemotaxin" (MOC), apparently a peptide with molecular weight of 10,000 which differs from GRAM was reported, (E. Kownatzki et al., Clin. Exp. Immunol. 64 [1986] 214–222). A neutrophil chemotactic factor produced by human blood monocytes stimulated with LPS, with a molecular weight of approximately 10,000 and an isoelectric point of 8–8.5 was also known (T. Yoshimura et al., *J. Immunol.* 139 [1987] 788–793). Finally it was also reported that rat peritoneal macrophages stimulated in culture with LPS release a selective neutrophil chemotactic factor (F. Q. Cunha et al., *J. Med. Biol. Res.* 19 [1986] 775–777 and *Eur. J. Pharmacol.* 129 [1986] 65–76).

Due to the preliminary nature of the biochemical information contained in these reports it is impossible to speculate about structural similarities and differences among the various factors described.

Subsequently to the priority date(s) which is (are) being claimed for the present invention, purification of a peptide probably corresponding to NAF was described by van Damme et al. (J. Van Damme et al., *J. Exp. Med.* 167 [1988] 1364–1376) and a sequence identical to that of NAF was reported by Gregory et al., (H. Gregory et al., *Biochem. Biophys. Res. Commun.* 151 [1988] 893–890) for a peptide that was purified from supernatants of lectin-stimulated human lymphocytes. The cDNA coding for MDNCF (T. Yoshimura et al., *Proc. Nat. Acad. Sci. USA* 84 [1987] 9233–9237) was recently cloned (K. Matsushima et al., *J. Exp. Med.* 167 [1988] 1883–1893) and found to correspond to the 3-IOC cDNA (J. Schmid and C. Weissmann, *J. Immunol.* 139 [1987] 250–256). Schmid and Weissmann have shown that the peptide encoded by the 3–10C cDNA has structural homology with platelet factor 4, beta-thromboglobulin, connective tissue-activating peptide III (CTAP-III) and interferon-gamma-inducible peptide (gamma-IP-10). These molecules are also homologous to a 73-residue peptide (MGSA) with melanoma growth-stimulating properties (A. Richmond et al., *EMBO J.* 7 [1988] 2025–2033) the sequence of which closely resembles that deduced from the gro-cDNA isolated from fibroblasts (A. Anisowicz et al., *Proc. Nat. Acad. USA* 84 [1987] 7188–7192). A murine macrophage-derived inflammatory protein (MIP), possibly related to the proteins described above, was also reported (G. Davatelis et al., *J. Exp. Med.* 167 [1988] 1939–1944) and appears to be a member of a family of peptides including RANTES, the 8 kd product of a cDNA isolated from IL-2 dependent, antigen-driven human T-cell clones (T. J. Schall et al., *J. Immunol.* 141 [1988] 1018–1029). The functions of these peptides are largely unknown. MGSA and CTAP-III (C. W. Castor et al., *Proc. Nat. Acad. Sci. USA* 80 [1983] 765–769) were reported to be mitogenic, and platelet factor 4 was shown to have immunomodulatory effects (A. D. Barone et al., *J. Biol. Chem.* 263 [1988] 8710–8715).

The results obtained suggest that NAF selectively activates neutrophils by a receptor-mediated process similar to that initiated by chemotactic agonists.

2. SUMMARY OF THE INVENTION

The NAF of this invention was found to induce oxygen radical formation and enzyme release in human neutrophils by acting via a selective receptor, different from all receptors thus far described.

The total amino acid sequence of NAF purified from LPS-stimulated human monocytes has been determined and a gene coding for the main NAF species synthesized and expressed as a recombinant peptide with the same neutrophil-activating properties as its natural homologue.

The invention thus concerns NAF and its isolation from natural sources such as human monocytes.

It also concerns synthetic, especially recombinant NAF and its preparation and expression.

3. DETAILED DESCRIPTION

The complete amino acid sequence of NAF was determined by known sequencing methods:

Ser-Ala-Lys-Glu-Leu-Arg-Cys-Gln-Cys-Ile-Lys-Thr-Tyr-Ser-Lys-Pro-Phe-His-Pro-Lys-Phe-Ile-Lys-Glu-Leu-Arg-Val-Ile-Glu-Ser-Gly-Pro-His-Cys-Ala-Asn-Thr-Glu-Ile-Ile-Val-Lys-Leu-Ser-Asp-Gly-Arg-Glu-Leu-Cys-Leu-Asp-Pro-Lys-Glu-Asn-Trp-Val-Gln-Arg-Val-Val-Glu-Lys-Phe-Leu-Lys-Arg-Ala-Glu-Asn-Ser.

Edman degradation of the full protein and of typtic fragments T 7–26 and T 27–47 obtained after splitting of SH-methylated and amino-succinylated NAF gave the sequence up to position 47. Upon hydrolysis with 75% formic acid and Edman degradation two approximately equimolar sequences of 20 amino acids were obtained, followed by a single pattern corresponding to the aminoterminal sequence of NAF beyond position 20. The sequence of the carboxyterminal peptide A 53–72 was determined by subtraction and confirmed by the analysis of the typtic peptide T 61–72. Carboxypeptidase- A and -B give no detectable cleavage product, but after treatment of 1 nmol NAF with carboxypeptidase Y 120 pmol serine are released, indicative of serine as the carboxyterminus.

Analysis of various batches of NAF revealed some aminoterminal heterogeneity. The above sequence is for the major component (about 70%), which is believed to be largely responsible for the biological activities. Three further variants could be identified:

Sequence 1 (about 17%):

Ala-Val-Leu-Pro-Arg-Ser-Ala-Lys-Glu-Leu-Arg-Cys-Gln-Cys-Ile-Lys-Thr-Tyr-Ser-Lys-Pro-Phe-His-Pro-Lys-Phe-Ile-Lys-Glu-Leu-Arg-Val-Ile-Glu-Ser-Gly-Proi.e the above full sequence further extended at the N-terminus by Ala-Val-Leu-Pro-Arg- (the full protein thus has 77 amino acids)

Sequence 2 (about 8%):

Lys-Glu-Leu-Arg-Cys-Gln-Cys-Ile-Lys-Thr-Tyr-Ser-Lys-Pro-Phe-His-Pro-Lys-Phe-Ile-Lys-Glu-Leu-Arg-Val-Ile-Glu-Ser-Gly-Proi.e. the above full sequence shortened at the N-terminus by Ser-Ala- (the full protein thus has 70 amino acids)

Sequence 3 (about 5%):

Glu-Leu-Arg-Cys-Gln-Cys-Ile-Lys-Thr-Tyr-Ser-Lys-Pro-Phe-His-Pro-Lys-Phe-Ile-Lys-Glu-Leu-Arg-Val-Ile-Glu-Ser-Gly-Pro-.

i.e. the above full sequence shortened at the N-terminus by Ser-Ala-Lys- (the full protein thus has 69 amino acids).

All these sequences can be aligned to the predicted sequence from the 3–10C cDNA, consisting of 99 amino acids (J. Schmid and C. Weissmann, *J. Immunol.* 139 [1987] 250–254). The major NAF peptide corresponds to positions 28 to 99 of the 3–10C amino acid sequence, while the three above variants start at positions 23 (sequence 1), 30 (sequence 2) and 31 (sequence 3) thereof.

Comparison of the 3–10C cDNA-derived sequence with the above sequence data suggests that mononuclear phagocytes synthesize a precursor of NAF which is processed intracellularly. The 77-residue peptide could represent the largest secreted form of NAF as it corresponds to the cDNA-derived sequence minus the predicted signal peptide of 22 amino acids. The main, 72-residue NAF species and the analogues with 70 and 69 residues may arise from further posttranslational modifications.

All forms of NAF have four cysteine residues expected to form intrachain disulfide bridges which appear important for activity since mercaptoethanol is found to be inhibitory (P. Peveri et al., *J. Exp. Med.* 167 [1988] 1547–1560). The disulfide bridges are likely to link the positions 7–34 and 9–50 as in beta-thromboglobulin and platelet factor 4 which are partially homologous to NAF.

In accordance with the homology to β-thromboglobulin NAF has two intramolecular disulfide bridges. Consequently the calculated molecular weight is 8384.7, clearly higher than the apparent molecular weight found by SDS-gel electrophoresis.

The production of NAF from natural sources, such as human monocytes, results in poor yields and requires extensive and complicated purification steps.

In order to produce NAF in larger amounts and better yield synthetic processes, e.g. total chemical synthesis or recombinant DNA processes, are indicated. The production of synthetic NAF, e.g. by recombinant DNA methods, including expression in a procaryotic or eucaryotic expression system, e.g. in E. coli are also part of the invention. Synthetic NAF, i.e. NAF produced by synthetic processes such as recombinant DNA processes, is also part of the invention. Synthetic NAF, e.g. the recombinant NAF isolated e.g. from bacteria has the same amino acid sequence(s) as natural NAF and the same biological properties and activities. "Recombinant NAF" means NAF obtained by recombinant DNA processes.

The preparation of NAF by recombinant DNA methods is effected according to known procedures, namely synthesis, purification and ligation of corresponding oligonucleotides, cloning of the synthetic NAF gene, expression in e.g. E. coli and finally recovery and purification of recombinant NAF. For example, a gene coding for the 72-amino acid NAF is synthesized, preferably with codon optimization, then cloned and expressed in E. coli.

Western blot analysis of crude bacterial extracts using an antiserum raised against natural NAF reveals a single band that comigrates with natural NAF. Recombinant NAF purified to homogeneity has identical amino- and carboxyterminal sequences as the 72-amino acid natural NAF. If tested on human neutrophils it is found to have the same activity and potency as natural NAF in inducing chemotaxis, a rapid rise in cytosolic free $Ca^{2+}$, activation of the respiratory burst, and release of specific and azurophil granule contents.

FIG. 13 shows the design of a synthetic NAF gene. Changes are apparent over the coding sequence of the 3–10C cDNA to facilitate expression in E. coli. At the 3'-end, the naturally-occurring terminator TAA is replaced by a triple terminator TAATAATGA, and a BamHI site is added immediately downstream. At the 5'-end, SphI and ClaI sites are added to allow insertion into the cloning and the expression vector, respectively. At base 34, a TaqI restriction site is created for later 5'-end manipulations by changing the Arg codon from AGA to CGA.

Figure 14:
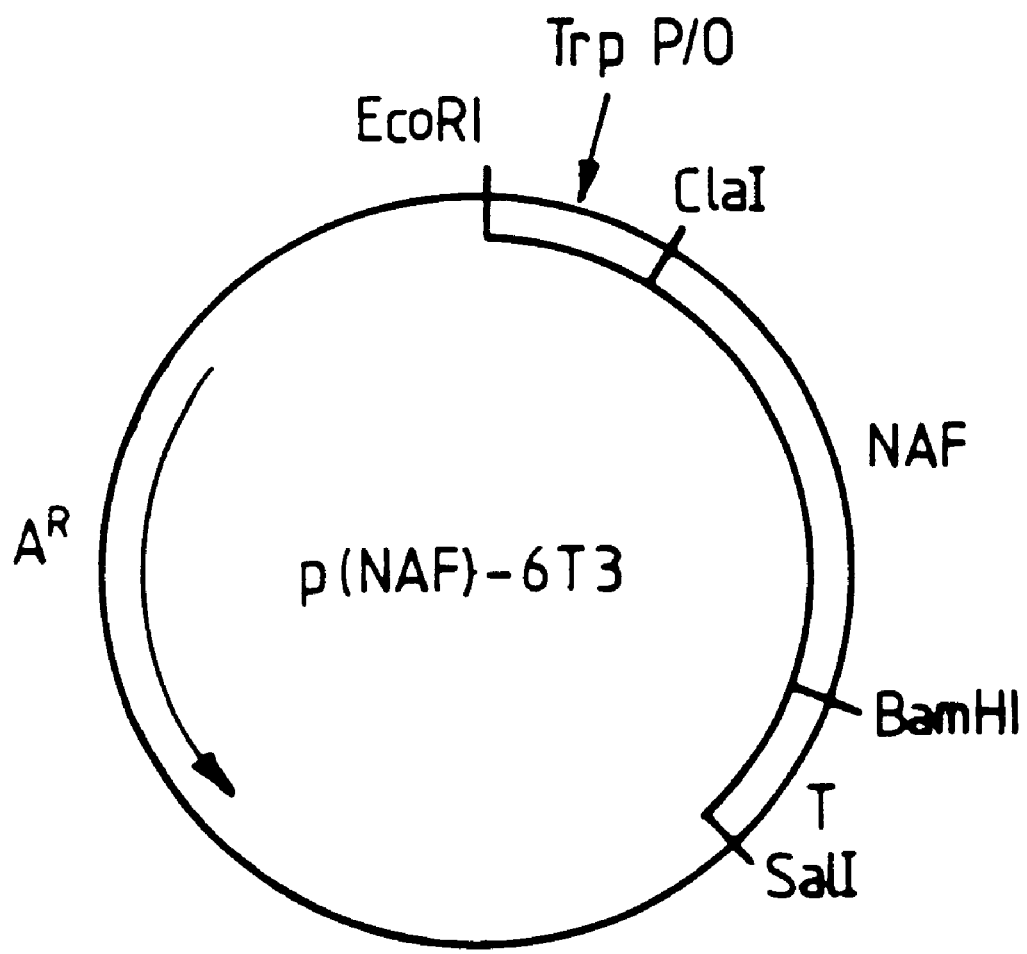

Blockwise annealing (oligonucleotides 1–2, 3–4 and 5–6) has no advantage over the simultaneous ligation of all six oligonucleotides. 5'-Phosphorylation of all oligonucleotides gives rise to ligation products larger than the expected size, but when the terminal oligonucleotides (1 and 6) are not phosphorylated, the product with the highest molecular weight is the complete gene with 248/240 bases. The gene is ligated into SphI/BamHI-cut pBS M13⁻ and transformed into E. coli. Plasmid DNA isolated from 6 of the resulting ampicillin-resistant colonies is cut with ClaI/BamHI, yielding in all cases a 237 bp band on a 1.4% agarose gel. DNA sequencing shows the clones containing the correct sequence. The ClaI/BamHI band from a correct clone is removed from the gel and cloned into the Trp promoter vector pIL402(Term). As a possible means of increasing expression, a synthetic transcription terminator (see Example 17) may be incorporated into this vector attached to the 3'-end of the human GM-CSF gene at the BamHI site. The NAF gene is therefore inserted between this BamHI site and the ClaI site downstream of the transcription initiation site in the promotor, to replace the GM-CSF gene. The resulting NAF expression plasmid, p(NAF)-6T3, is shown in FIG. 14.

Silver stain and western blot analysis of extracts of indole acrylic acid-induced E. coli containing p(NAF)-6T3 demonstrates the time-dependent production of a peptide that comigrates with natural NAF and reacts with an antiserum against natural NAF.

The above expression system can also be used to prepare the NAF variants mentioned above or other biologically active NAF fragments such as amino-truncated NAF fragments.

The biological properties of NAF are species-specific. Activity in the rabbit most closely mirrors activity in humans. Preliminary tests in the mouse, rat and guinea pig have not shown any clear activity.

NAF is indicated for use in the treatment of conditions which are accompanied or caused, locally or systemically, by a modification of the number or activation state of the PMN (polymorphonuclear cells—neutrophils). NAF extensively modifies these PMN parameters and is therefore indicated for use in the treatment of conditions in which an elevation of the number or activation state of the PMN leads to clinical improvement, e.g. in bacterial, mycoplasma, yeast, and fungal, in and in viral infections. Furthermore NAF is indicated for use in inflammatory illnesses such as psoriasis, arthritic conditions and asthma, or in conditions of abnormally low neutrophil count and/or generalized low neutrophil level, and in the preparation of antagonists for use in these indications.

3. DESCRIPTION OF THE FIGURES

FIG. 1: NAF production induced by LPS:

Mononuclear cells separated as described in Example 1 are seeded in 24-well culture plates ($5 \times 10^6$ cells in 1 ml) and stimulated with LPS at the concentrations indicated. At various time intervals the media are collected, cleared by centrifugation (20000 rpm for 20 min. at 4° C.) and NAF activity is measured. Cells from a single donor; means of duplicate cultures. These results are representative of 4 similar experiments using cells of different donors.

Figure 2:
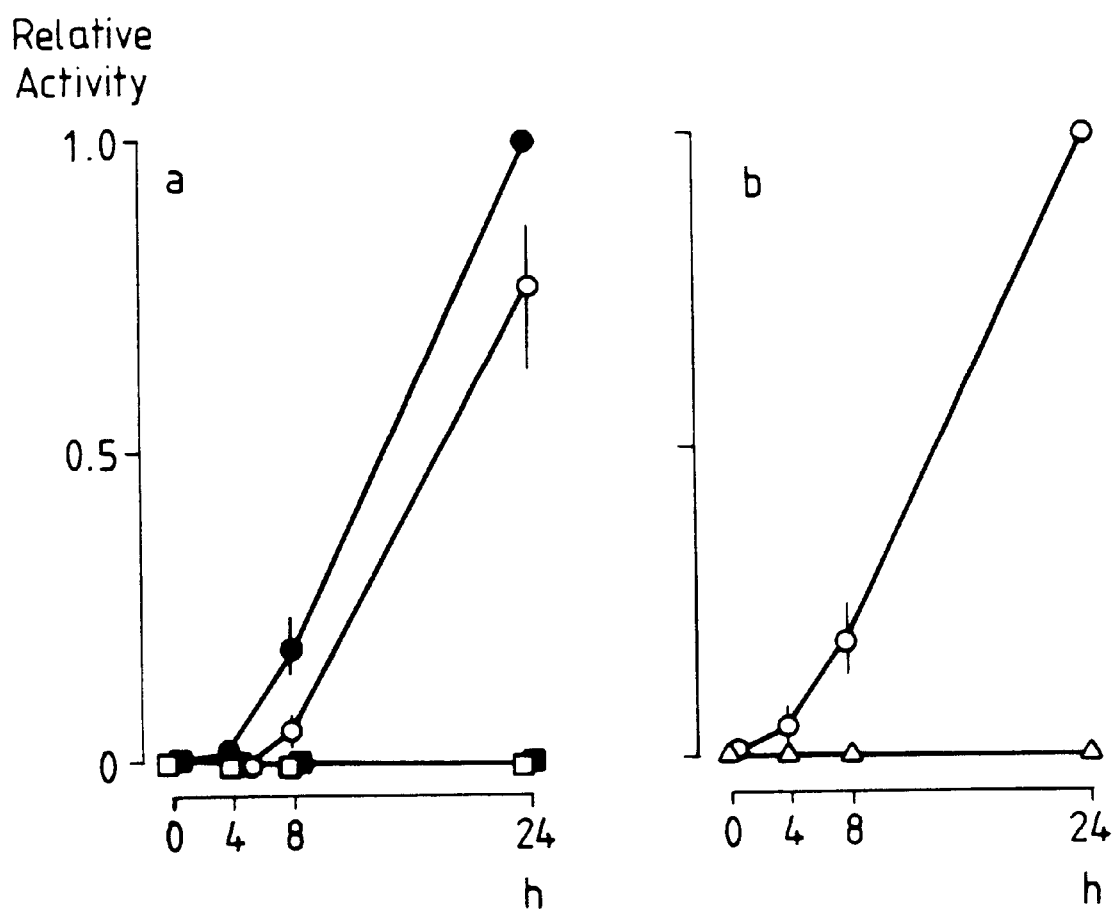

FIG. 2: production of NAF by mononuclear phagocytes but not by lymphocytes:

a) The total mononuclear cell fraction (●,■,$5 \times 10^6$ cells/ml) and adherent cells derived therefrom (○,□) are cultured in the presence (●,○) and absence (■,□) of 100 ng LPS for 24 h.

b) Monocytes (○, $10^6$ cells/ml) and lymphocytes (Δ,$4 \times 10^6$ cells/ml) purified by elutriation are cultured in the presence of 100 ng LPS.

Graphs represent mean relative values for elastase release from 5(a) and 6(b) separate experiments each run in duplicate. The data are normalized by setting the 24 h value of ● in panel a and ○ in panel b equal to 1.0 and calculating the other values (mean ± S.D.) relative to it. This type of representation is chosen in order to account for the individual variation in NAF production on the one hand and in responsiveness of the neutrophils used to test NAF on the other.

Figure 3:
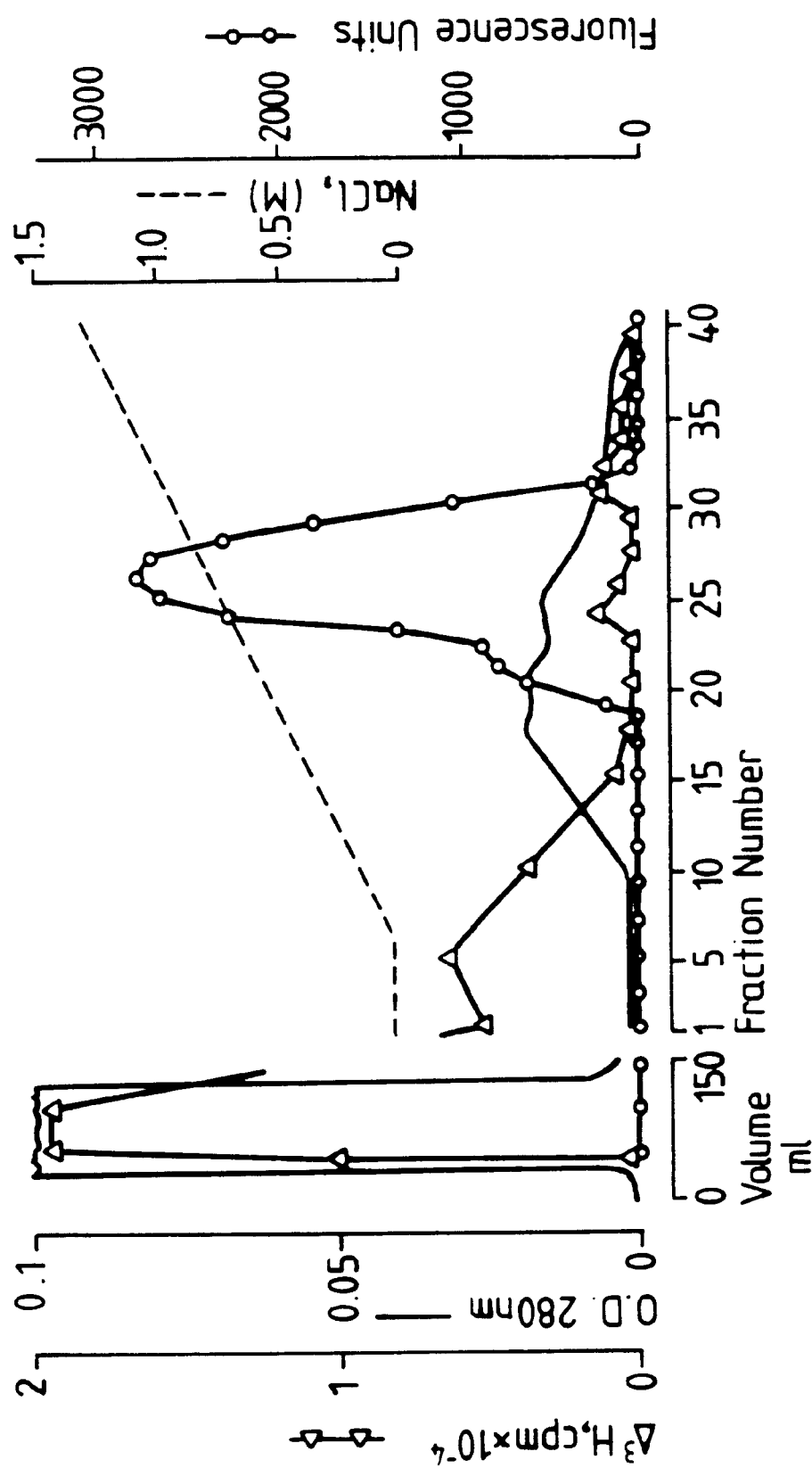

FIG. 3: partial purification of NAF by phosphocellulose chromatography:

The distribution of protein (absorbance at 280 nm , - - - ), NAF (○) and IL-1 (Δ) is shown. The fractions with the highest NAF activities are pooled as indicated.

Figure 4:
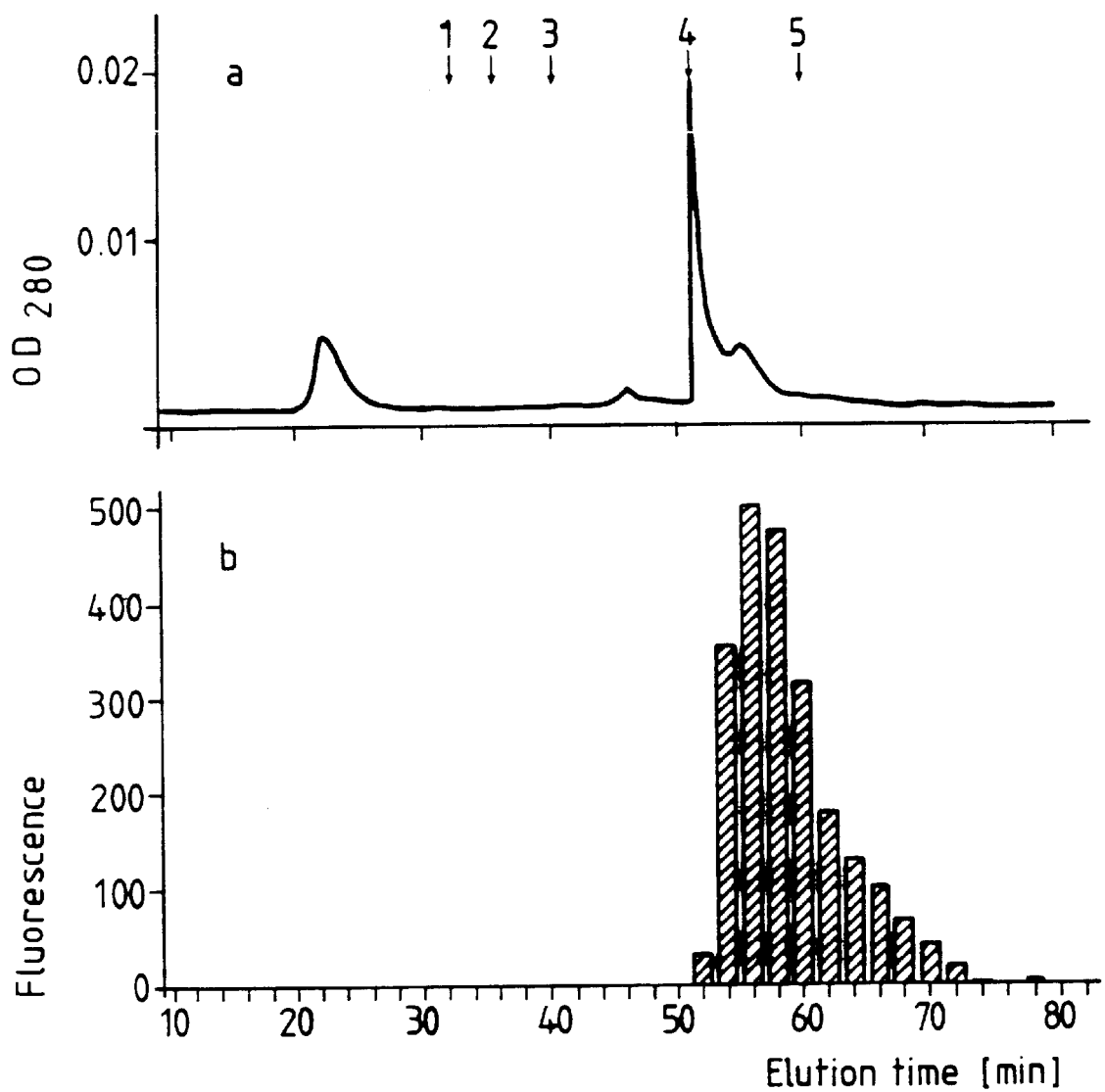

FIG. 4: purification of NAF by HPLC gel filtration:

a) Distribution of protein (absorbance at 280 nm) and elution times of molecular weight markers (arrows: 1=MW 66200; 2=MW 42700;3=MW 21500;4=MW 6500 and 5=MW 1255).

b) Profile of NAF activity.

Figure 5:
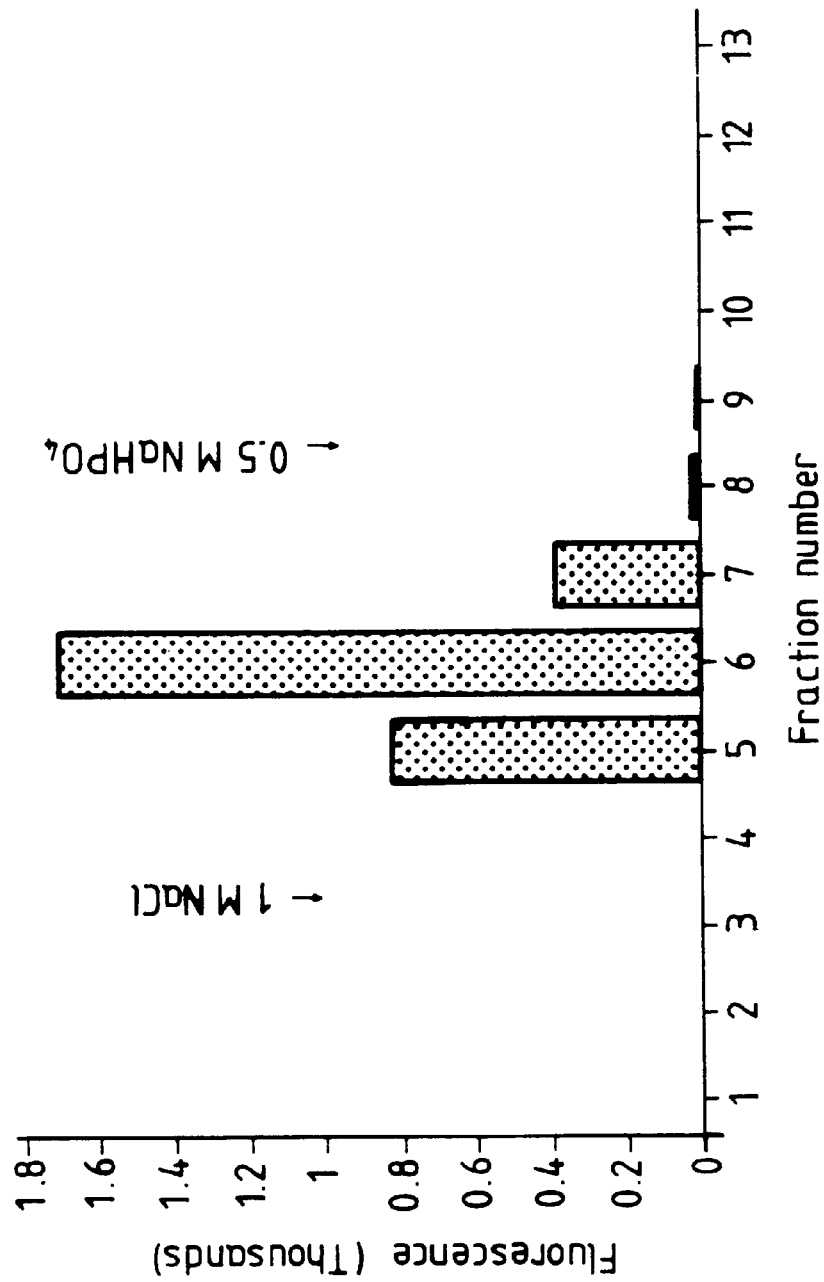

FIG. 5: purification of NAF by chromatography on hydroxylapatite:

Partially purified NAF is loaded onto the column at low salt concentration and then eluted by a buffer containing 1 M NaCl. Bars show NAF activity.

Figure 6:
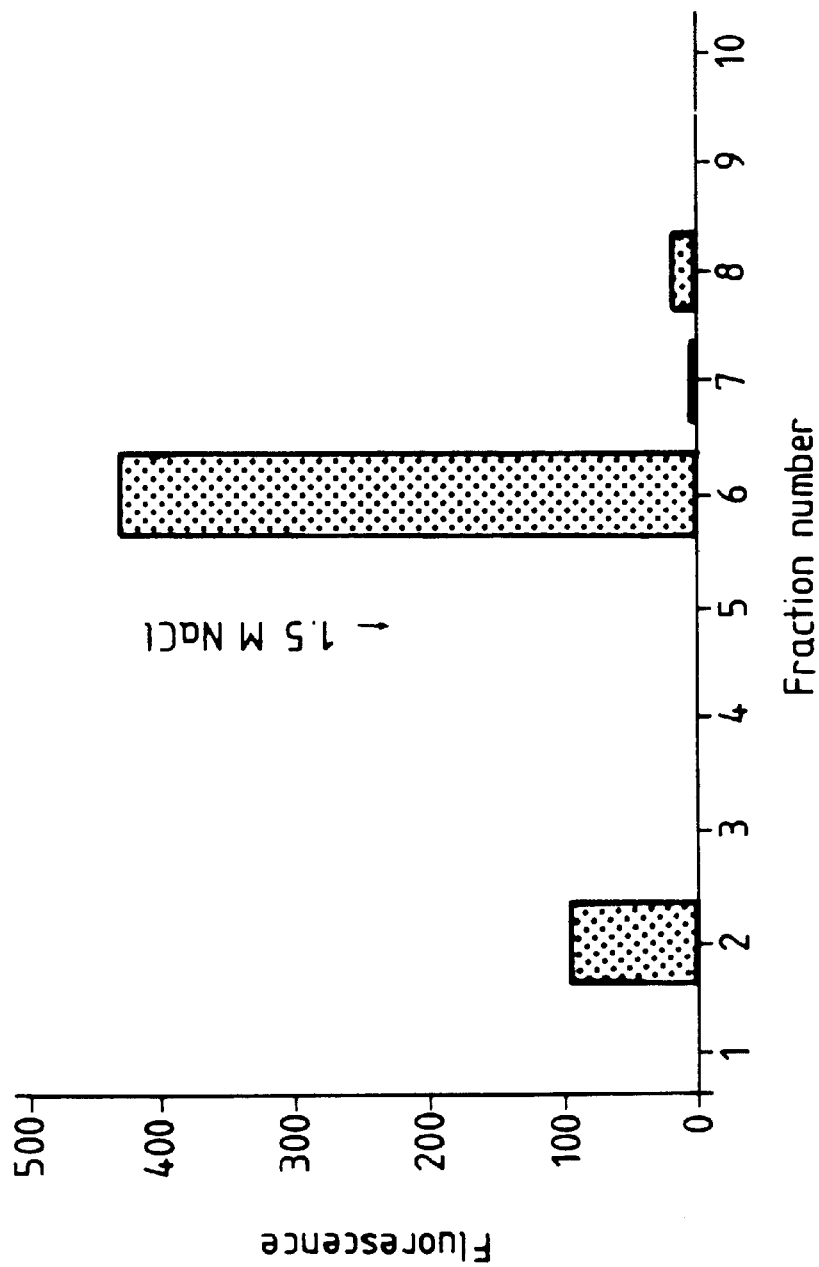

FIG. 6: purification of NAF by chromatography on heparin-Sepharose:

Partially purified NAF is loaded onto the column at low salt concentration and then eluted with a buffer containing 1.5 M NaCl. Bars show NAF activity.

Figure 7:
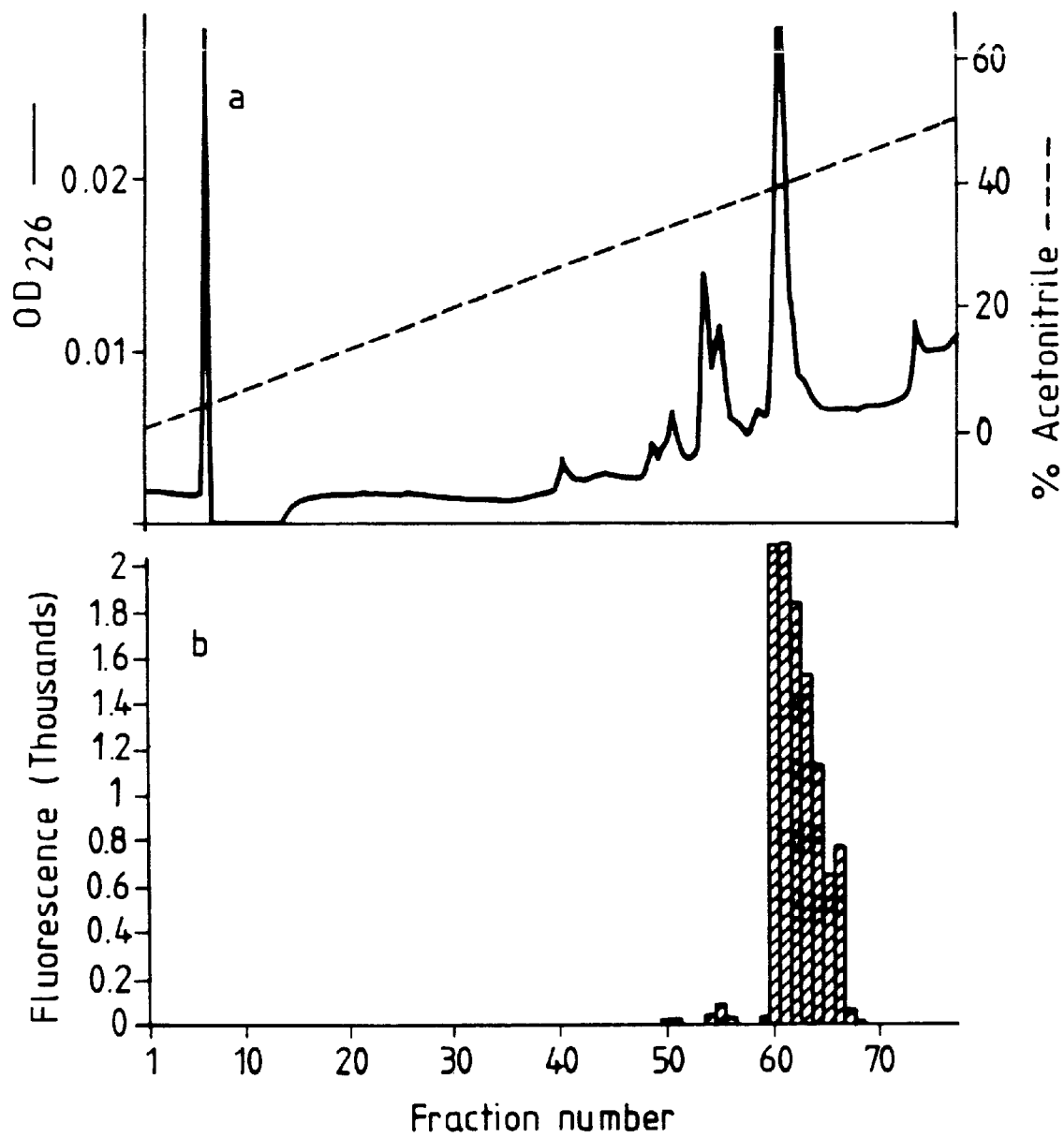

FIG. 7: purification of NAF by reversed-phase HPLC on a C4 column:

a) Purified NAF is loaded onto a RP column in 0.1% trifluoroacetic acid. The column is developed with a linear gradient of acetonitrile in 0.1% trifluoroacetic acid.

b) Bars show NAF activity.

Figure 8:
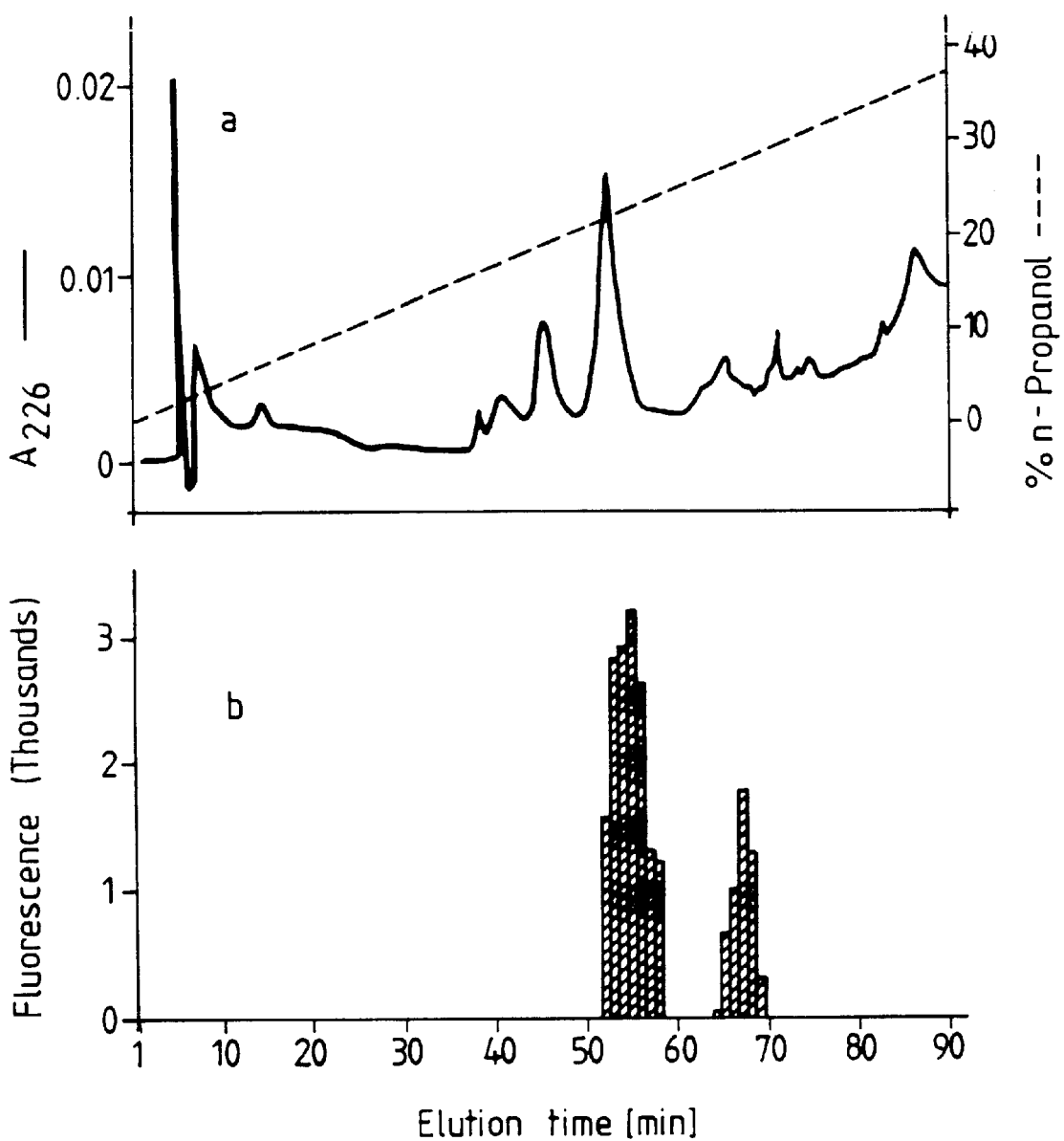

FIG. 8: purification of NAF by reverse-phase HPLC on a CN-propyl column:

a) Purified NAF is loaded onto a Bakerbond CN-propyl column in 0.1% trifluoroacetic acid. The column is developed with a linear gradient of n-propanol in 0.1% trifluoroacetic acid.

b) Bars show NAF activity.

Figure 9:
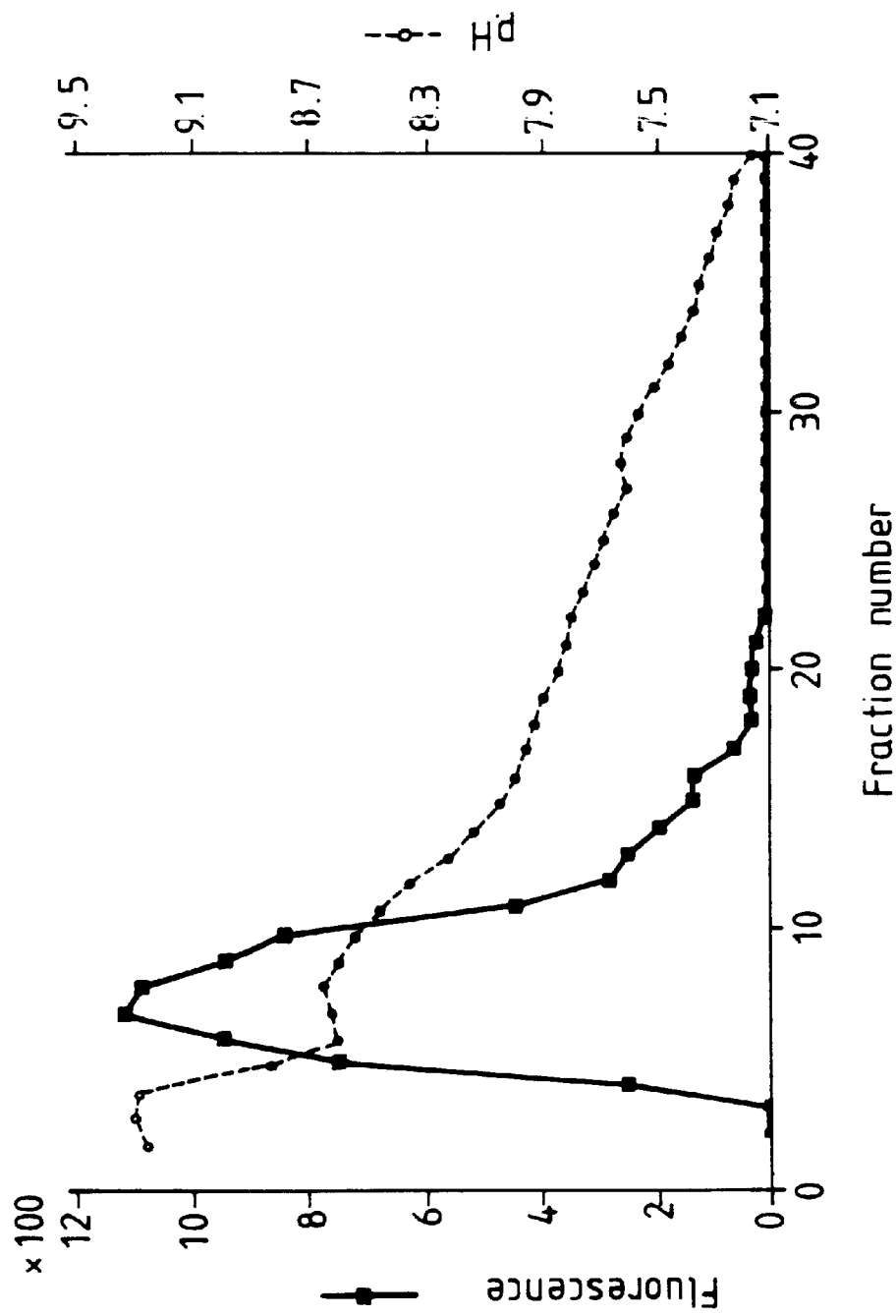

FIG. 9: purification of NAF by chromatofocusing:

Partially purified NAF is loaded onto a chromatofocusing column. The column is developed with polybuffer 96-HCl, pH 7.0. Fractions are tested for NAF activity (—●—) and for pH (—◆—)

Figure 10:
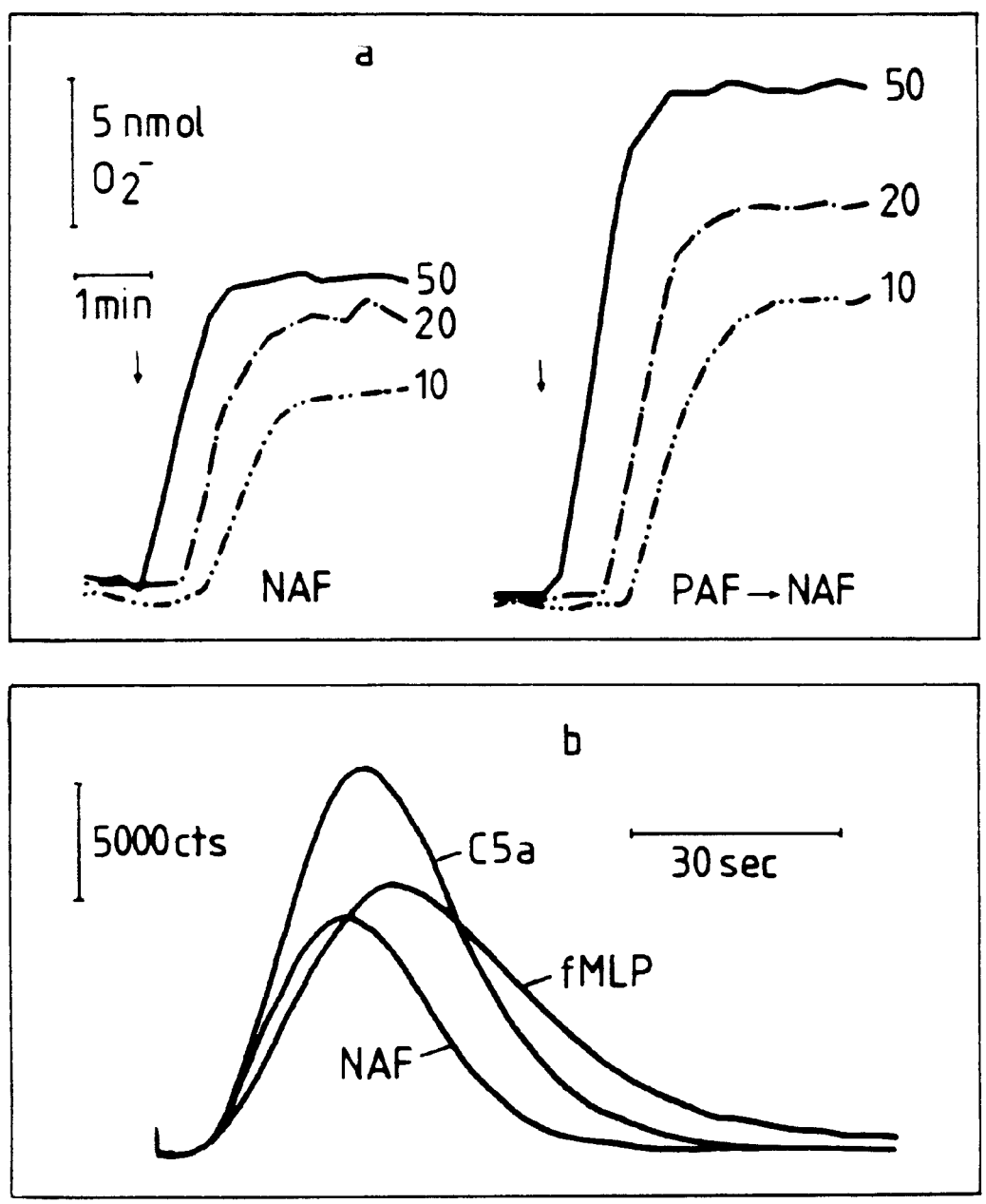

FIG. 10: respiratory burst response to partially purified NAF:

a) Superoxide production: neutrophils ($3\times10^6$ /ml) are preincubated at 37° with or without 1 μm PAF for 2 minutes and then stimulated with increasing amounts of NAF. Recordings of cytochrome c reduction following NAF addition are shown.

b) $H_2O_2$-dependent chemiluminescence: the progress curves following stimulation with partially purified NAF and approximately equiactive concentrations of C5a and fMLP are shown on the left. The initial phase of the response is detailed on the right. The stimulants are added in 50 μl of PBS-BSA.

Figure 11:
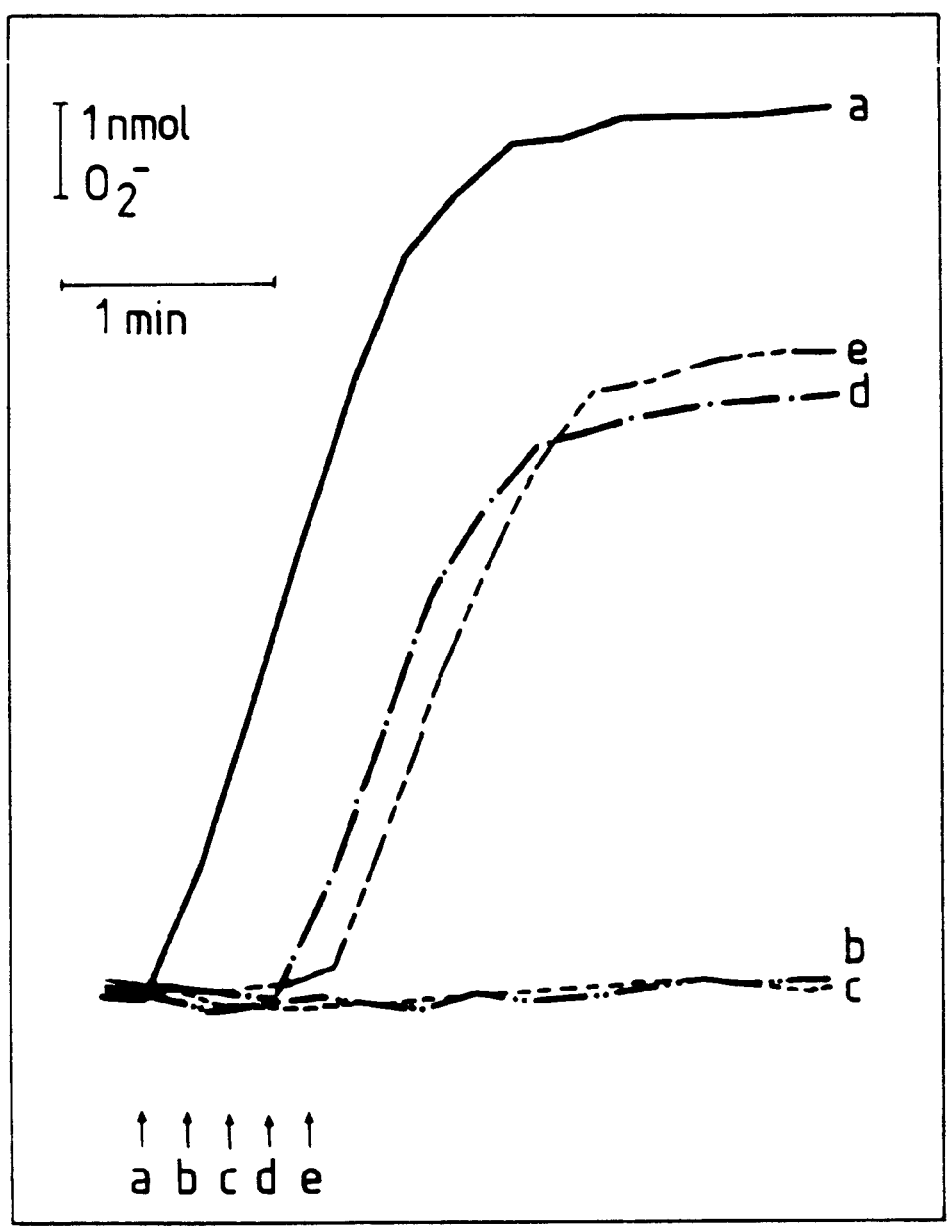

FIG. 11: discrimination between NAF and C5a:

C5A and NAF are incubated for 15 minutes with fresh human serum or with PBS and the activity of the preparations is determined (superoxide production).

a) C5a in PBS, b) C5a in serum, c) serum alone, d) NAF in PBS, e) NAF in serum.

Figure 12:
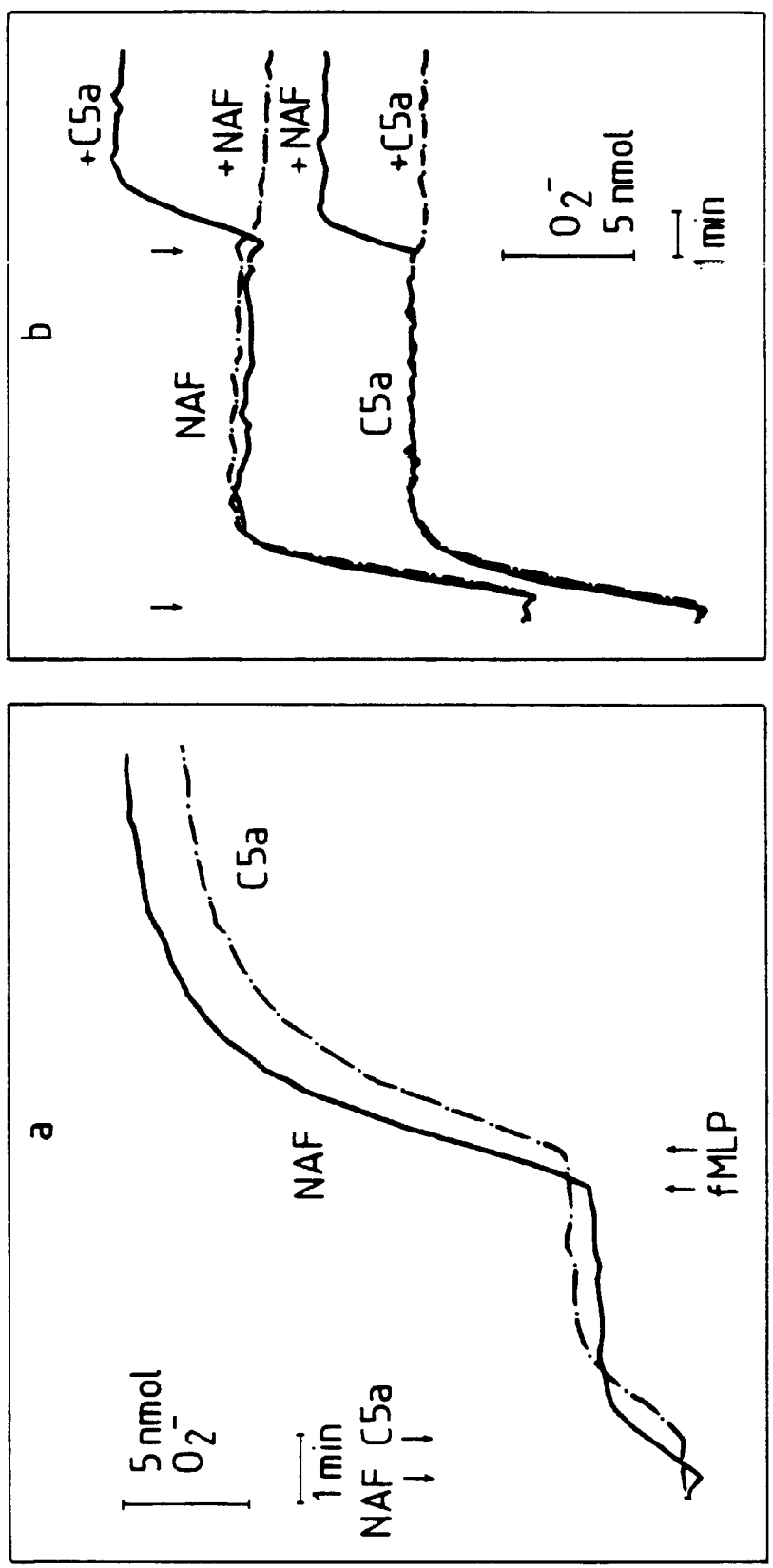

FIG. 12: superoxide formation in response to sequential stimulation with partially purified NAF, C5a and fMLP:

a) Neutrophils ($3\times10^6$ /ml) are preincubated at 37° C. for 5 min. and then stimulated with different agonists as indicated (arrows).

b) Sequential or repeated stimulation with NAF and C5a. Conditions as in a).

Arrows show addition of agonists as indicated. The concentration of C5a is 0.5 nM in a) and 0.2 nM in b), that of fMLP is 20 nM in both experiments. The agonists are added in 50 μl of PBS-BSA.

FIG. 13: nucleotide sequence of synthetic NAF gene:

The single oligonucleotides, ON-1 to ON-6, used for building the gene are shown by broken lines. The (underlined) nucleotide numbers appear on the right-hand side above the double strand. The corresponding peptide sequence of the major form is numbered starting at the aminoterminal end (Ser). The ClaI and BamHI restriction sites are indicated above the double strand. The TaqI site created by substituting a C for the A in the arginine codon is also shown.

FIG. 14: expression vector p(NAF)-6T3:

$A^R$=ampicillin resistance gene

Trp P/O=tryptophan promoter

T=synthetic transcription terminator

Figure 15:
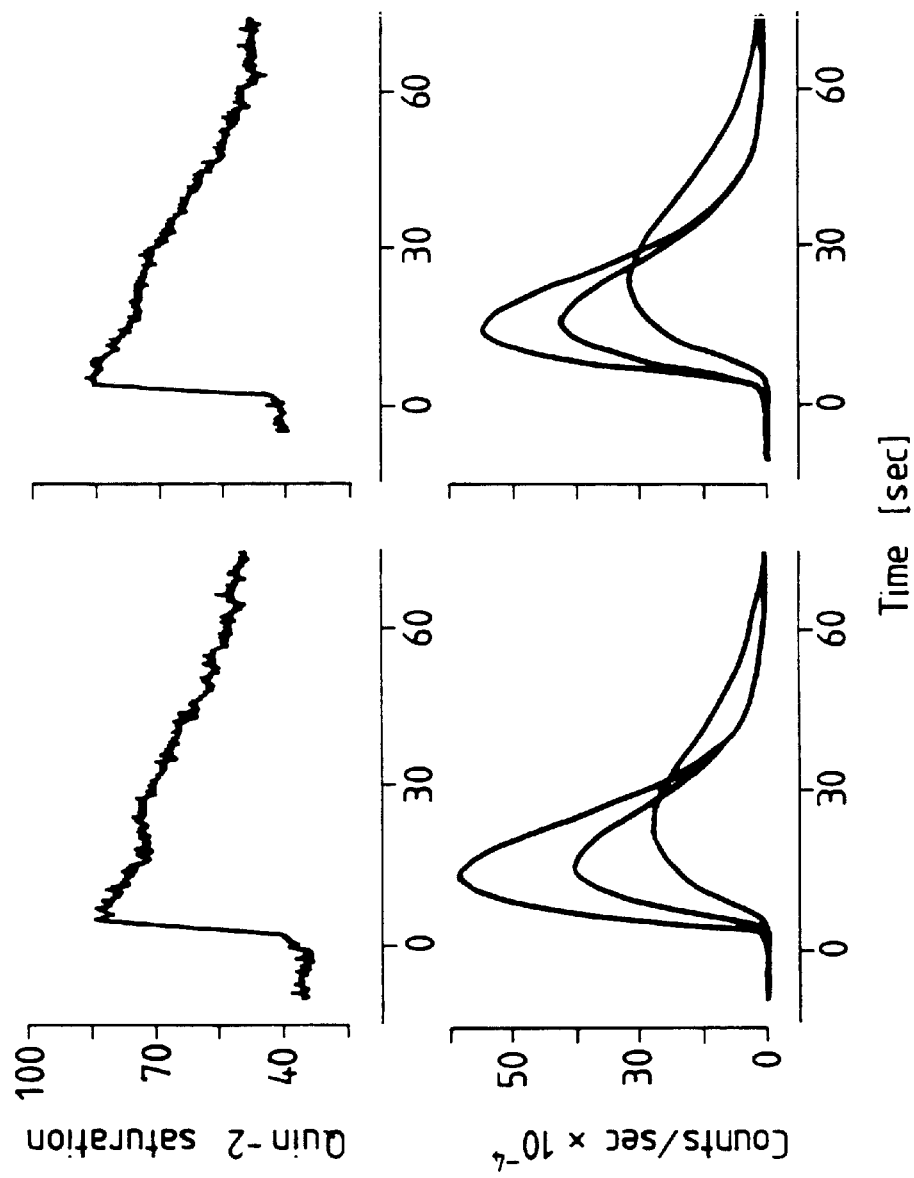

FIG. 15: identity of natural and recombinant NAF

Upper graphs: cytosolic free $Ca^{2+}$ changes induced by natural (left) and recombinant (right) NAF. Neutrophils ($4\times10^6$ cells/ml) are loaded with 0.1 nmol quin-2/AM and then stimulated with 3 nM NAF (mark). Quin-2 saturation changes calibrated as described in V. Von Tscharner et al., *J. Biol. Chem.* 261 (1986) 10163–10168.

Lower graphs: respiratory burst induced by natural (left) and recombinant (right) NAF. Neutrophils ($10^6$ cells/ml) are stimulated with 3, 10 and 30 nM NAF at time zero and hydrogen peroxide production is measured by chemiluminescence (M. P. Wymann et al., *Anal. Biochem.* 165 [1987] 371–378).

Figure 16:
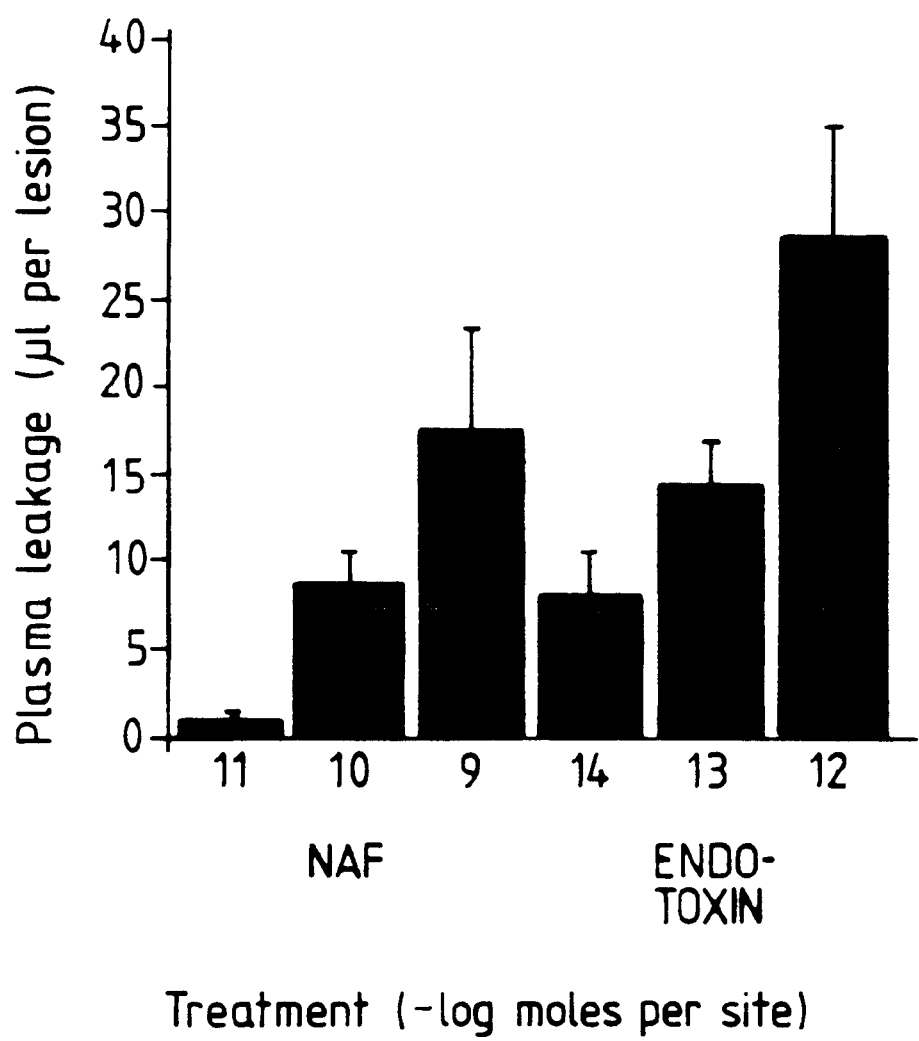

FIG. 16: plasma leakage into skin sites:

Following intradermal injection of NAF or endotoxin; duration: 4 hours;

mean ± standard errors of the average response of 3 rabbits.

Figure 17:
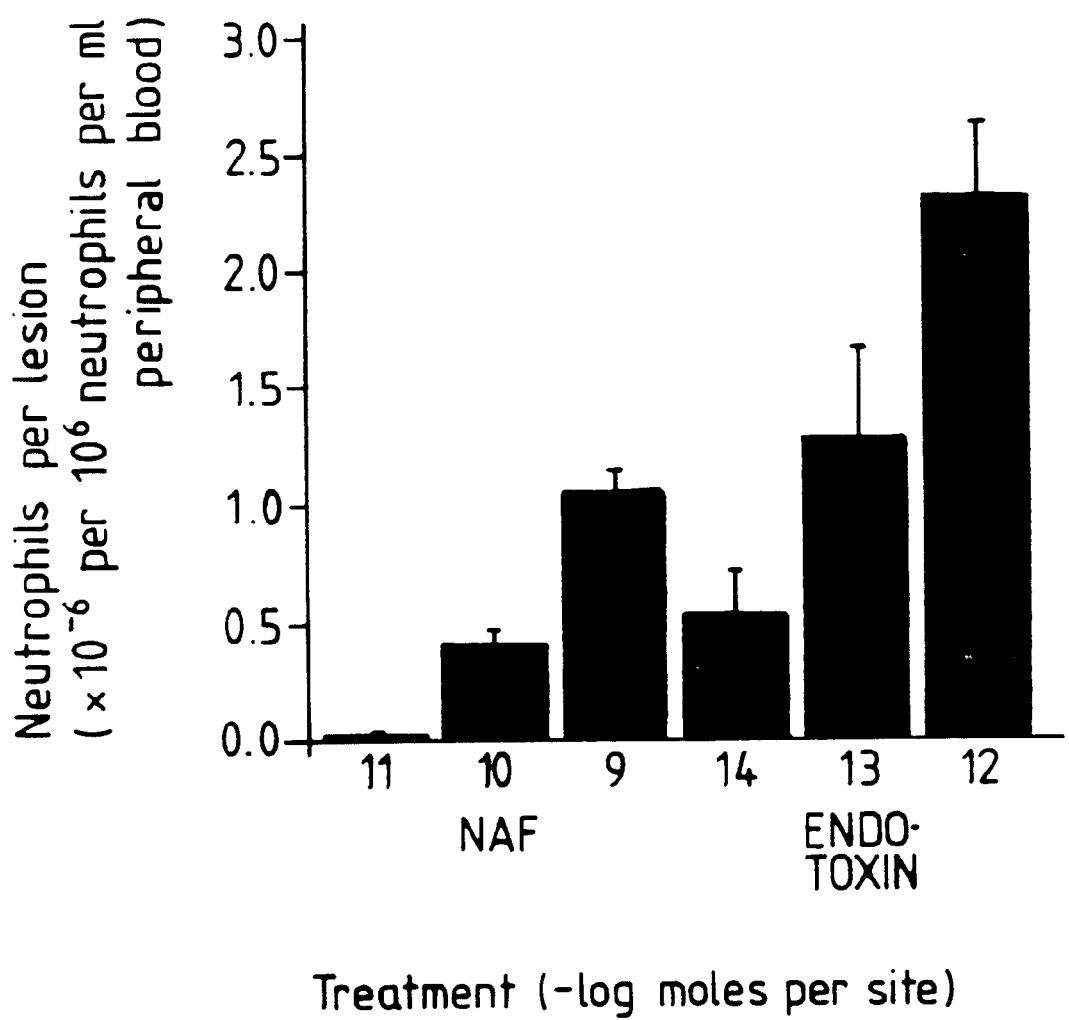

FIG. 17: neutrophil accumulation in skin sites:

Measurement simultaneously with the responses plotted in FIG. 16.

Figure 18:
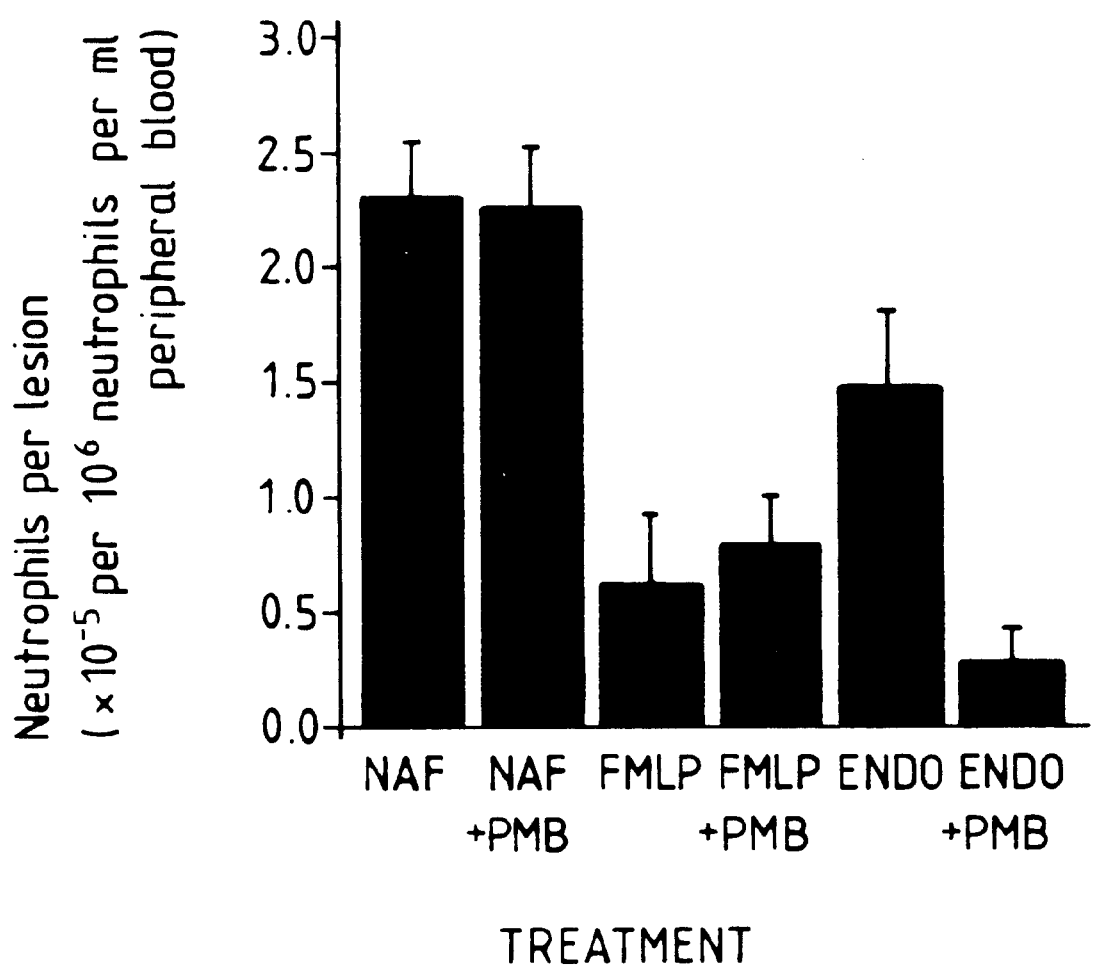

FIG. 18: effect of polymyxin B on neutrophil accumulation:

Following intradermal injection of NAF ($10^{-9}$ moles/site), fMLP ($10^{-9}$ moles/site) or endotoxin ($10^{-13}$ moles/site);

Polymyxin B: 40 μg/site;

duration: 2 hours;

mean ± standard errors of the average responses of 3 rabbits.

Figure 19:
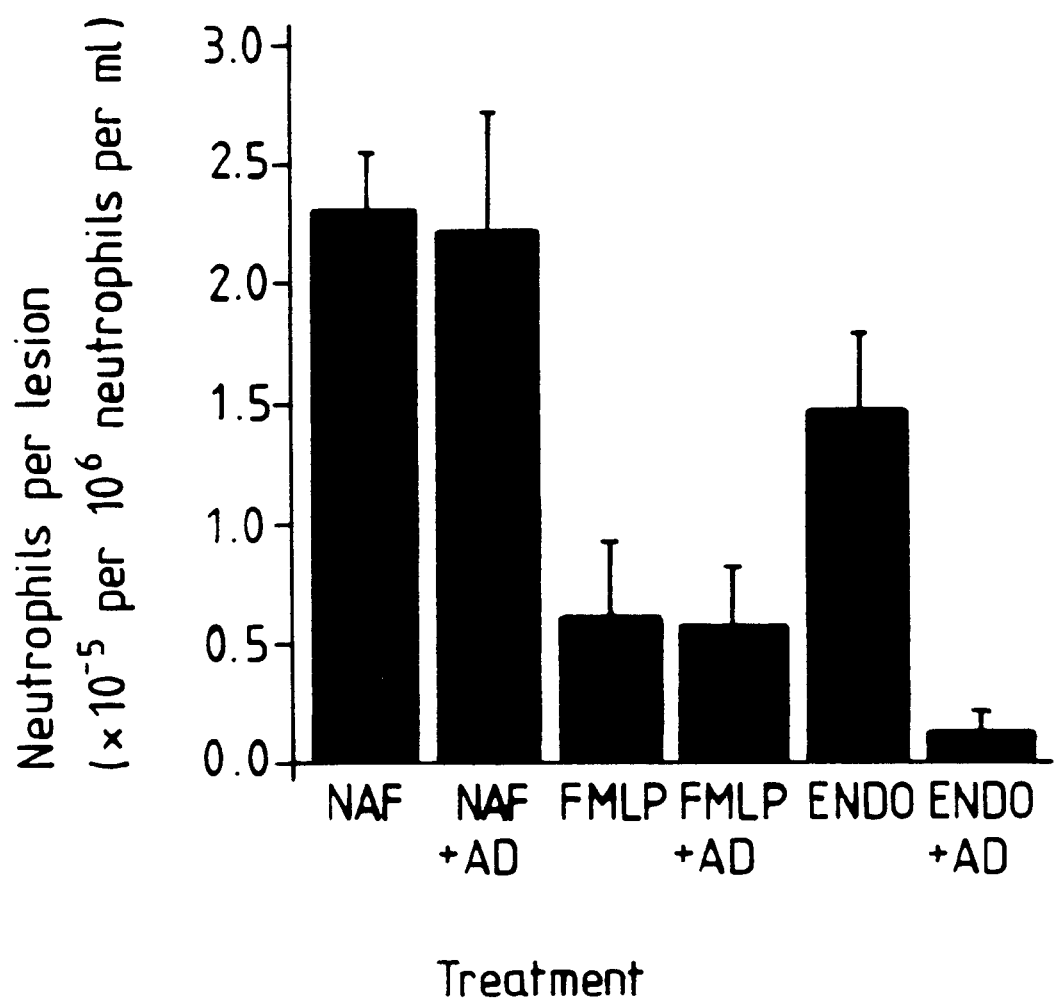

FIG. 19: effect of actinomycin D on neutrophil accumulation:

Following stimulation of skin sites with NAF ($10^{-9}$ moles/site), fMLP ($10^{-9}$ moles/site) or endotoxin ($10^{-13}$ moles/site);

duration: 2 hours;

mean ± standard errors of the average responses of 3 rabbits.

5. EXAMPLES

The following Examples illustrate the invention. All temperatures are in degrees Centigrade. The following abbreviations are employed:

PHA     phytohemagglutinin
ConA    concanavalin A

-continued

| | |
|---|---|
| LPS | E. coli lipopolysaccharide |
| BSA | bovine serum albumin |
| fMLP | N-formyl-L-methionyl-L-leucyl-L-phenylalanine |
| PAF | 1-0-hexadecyl-2-0-acetyl-sn-glycero-3-phosphocholine (platelet-activating factor) |
| MEM | Eagle's minimal essential medium (Seromed GmbH, Munich, FRG), supplemented with 25 μg/ml neomycin, buffered to pH 7.4 with 25 mM NaHCO$_3$ and 20 mM HEPES |
| MEM-PPL | as above, containing in addition 1% pasteurized plasma protein solution (5% PPL-SRK, Swiss Red Cross Laboratory, Bern, Switzerland) and 100 IU/ml penicillin and streptomycin (Gibco A. G., Basle, Switzerland); |
| PBS | phosphate-buffered saline without Ca$^{2+}$ and Mg$^{2+}$ (137 mM NaCl, 2.7 mM KCl, 8.1 mM NaH$_2$PO$_4$ and 1.5 mM KH$_2$PO$_4$, adjusted to pH 7.4) |
| PBS-BSA | PBS supplemented with 0.9 mM CaCl$_2$, 0.49 mM MgCl$_2$ and 2.5 mg/ml BSA. |
| HEPES | N-2-hydroxyethylpiperazine-N'-2-ethanesulphonic acid |
| PPL-SRK | plasma protein solution (Swiss Red Cross) |
| NAF | neutrophil-activating factor or protein |
| CX | cycloheximide |
| IL-1 | interleukin-1 |
| SOD | superoxide |
| C5a | anaphylatoxin |
| CPC | controlled porous glass |
| PAGE | polyacrylamide gel electrophoresis |
| GM-CSF | granulocyte-macrophage colony-stimulating factor |
| CB | cytochalasin B (5 μg/ml) |
| MES | 2-[N-morpholino]ethanesulphonic acid |
| HPLC | high pressure liquid chromatography. |
| SDS | sodium dodecyl sulphate |

PART I

NAF Production by Human Monocytes

Example 1

Production of NAF by Human Monocytes Stimulated with LPS

Human monocytes are isolated from buffy coats of donor blood (Swiss Red Cross Laboratory, Bern, Switzerland) by centrifugation through a Ficoll-Paque gradient. This method separates neutrophils from the so-called mononuclear cells, a mixture of monocytes (about 20%) and lymphocytes (about 80%). Three monocyte preparations are used: (i) the total mononuclear cell fraction, (ii) monocytes enriched from the mononuclear cell fraction by adherence, and (iii) 90% pure monocytes separated from the lymphocytes by centrifugal elutriation (G. Garotta et al., *Biochem. Biophys. Res. Comm.* 140 [1986] 948–954 and K. J. Clemetson et al., *J. Exp. Med.* 161 [1985] 972–983). The cells are cultured in MEM-PPL and stimulated with increasing concentrations (0.1 ng to 1 μg/ml) of LPS. At different times, aliquots of the culture media are sampled and NAF activity is determined as the capacity to induce the release of elastase from human neutrophils pretreated with cytochalasin B (B. Dewald et al., *Biochem. Pharmacol.* 36 [1987] 2505–2510).

Mononuclear cell cultures (5×10$^6$ cells/ml) consisting of monocytes and lymphocytes in a ratio of approximately 1:5 produce NAF when stimulated with LPS (100 ng/ml). NAF accumulates in the medium over 24 h and the production levels off between 24 h and 48 h. No NAF is formed in the absence of stimulus. FIG. 1 shows the time course and concentration dependence of the effects of LPS which is already active between 0.1 ng/ml and 1 ng/ml.

The source of NAF is studied using different mononuclear cell preparations. FIG. 2a shows the LPS-dependent generation of NAF by the total mononuclear cell fraction and the monocytes selected therefrom by adherence. These results confirm that NAF production is dependent on LPS and indicate that NAF is produced by the monocytes. The presence of lymphocytes does not appear to influence the amount of NAF production. Similar results are obtained with monocytes and lymphocytes purified by elutriation. As shown in FIG. 2b, NAF is produced by the monocytes but not by the lymphocytes.

Example 2

Production of NAF by Human Monocytes Stimulated with PHA or ConA

The mononuclear cell fraction from human blood buffy coat, separated as described in Example 1, are cultured under the conditions outlined in Example 1 and stimulated with PHA (5 μg/ml) or ConA (10 μg/ml). The time course of NAF production is similar to the one observed with mononuclear cells stimulated with 100 ng/ml LPS. A maximum is reached after about 24 h.

Example 3

Inhibition of NAF Production by Cycloheximide

The fact that NAF is not released immediately upon stimulation of the monocytes, but rather in a time period of hours, depending on stimulus concentration, suggests that de novo protein synthesis is required, and that NAF production is actually induced by the stimulus. The requirement of protein synthesis is demonstrated by experiments in which NAF production is inhibited by the addition of cycloheximide. The results of a representative experiment are shown in Table 1.

TABLE 1

Inhibition of NAF production by cycloheximide

| Treatment | mean production of NAF after | | |
|---|---|---|---|
| | 4 h | 8 h | 24 h |
| None | 0 | 0 | 0 |
| LPS | 726 | 2042 | 2633 |
| LPS + CX | 0 | 0 | 0 |
| LPS + CX at 4 h | 774 | 966 | 639 |
| LPS + CX at 8 h | 752 | 1884 | 1854 |

Cycloheximide (CX, 10 μg/ml) is added 4 or 8 h after LPS (100 ng/ml). Activity is presented in fluorescence units, expressing elastase release.

PART II

NAF Purification

Example 4

Separation of NAF and IL-1 by Phosphocellulose Chromatography

Mononuclear cells obtained from donor blood buffy coats as described in Example 1 are cultured in MEM-PPL for 48 h in the presence of 100 ng/ml LPS in stirred culture bottles (1.5 liter, 5×10$^6$ cells/ml). The culture supernatants are then collected, centrifuged at 20000 rpm for 20 min. at 4° to remove particulate material, and loaded onto a 10 ml phosphocellulose column (Whatman P11, 1,4×6 cm) equilibrated with 20 mM potassium phosphate buffer, pH 7.2 containing 20 mM NaCl and 5% glycerol. The column is washed with 30 ml of the above buffer and then eluted with 90 ml of a linear NaCl concentration gradient (0.02 M to 1.5 M) in the same buffer. Fractions of 2 ml are collected in 0.1% polyethylene glycol and tested for NAF and IL-1 activity. Absorbance at 280 nm is monitored continuously as a measure of protein.

FIG. 3 shows the distribution profiles of protein (absorbance at 280 nm) and two biological activities, elastase release as a measure of NAF activity and thymocyte proliferation as a measure of IL-1 activity. Most of the protein as well as the IL-1 activity are recovered in the flow-through volume. Elution with a linear NaCl gradient yields some IL-1 activity at low ionic strength followed by a peak of elastase-releasing activity corresponding to NAF, which starts to elute at 0.5 M and reaches its maximum at 0.8 M NaCl. The peak is symmetric and is preceded by a small shoulder. Some UV-absorbing material is eluted by the salt gradient; its profile, however, does not coincide with the biological activities determined. As indicated in FIG. 3, IL-1 and NAF can be resolved completely. There is no elastase-releasing activity in association with IL-1 and no thymocyte proliferation-inducing activity in association with NAF. The recovery of NAF upon fractionation is nearly 100%, suggesting that the media do not contain inhibitors or activators.

Example 5

Purification of NAF Gel Filtration

A sample of 200 µl of NAF partially purified by phosphocellulose chromatography (Example 4) is applied onto a HPLC TSK- G2000 SW column (7.5×600 mm) with a TSK-GSWP precolumn (7.5×75 mm). The column is run in 100 mM $NaHPO_4$, pH 7.0 containing 100 mM NaCl, at a rate of 0.5 ml/min. Bovine serum albumin (MW 66200), ovalbumin (MW 42700), soybean trypsin inhibitor (MW 21500), aprotinin (MW 6500) and actinomycin D (MW 1255) are used as calibration standards. NAF elutes with a slightly asymmetric peak just after aprotinin and well above actinomycin D. The apparent molecular weight of NAF is therefore approximately 6500. No NAF activity is eluted before or after the described peak (FIG. 4).

Example 6

Purification of NAF by Hydroxylapatite

A pool of fractions obtained from phosphocellulose chromatography (Example 4) with a total volume of 15 ml (corresponding to approximately 800 ml of unfractionated culture supernatant) is diluted 1:10 with loading buffer (10 mM sodium phosphate, pH 6.9 in 0.1% polyethylene glycol 6000) and loaded onto a 3 ml hydroxylapatite column (Biogel HTP) equilibrated in loading buffer. The column is washed with three 3-ml portions of the loading buffer and then eluted with loading buffer supplemented with 1 M NaCl. By this procedure NAF is recovered from the column. Subsequent elution with 0.5 M sodium phosphate buffer, pH 6.9 does not yield any further NAF activity (FIG. 5).

Example 7

Purification of NAF by Heparin-Sepharose

A sample of 1 ml of NAF partially purified by phosphocellulose chromatography (Example 4) is loaded onto a 0.5 ml column of heparin-Sepharose 4B equilibrated in 10 mM sodium phosphate, pH 7.3 supplemented with 0.1% polyethylene glycol 6000 and 50 mM NaCl. The column is washed with the same buffer and then eluted with 10 mM sodium phosphate, pH 7.3 supplemented with 1.5 M NaCl. A minor amount of NAF is detected in the flow-through fluid upon washing of the column, but most of the activity bound to the column is eluted with the higher ionic strength buffer (FIG. 6).

Example 8

Purification of NAF by Reverse-Phase High Pressure Liquid Chromatography on a C4 Column A sample of NAF purified by phosphocellulose chromatography (Example 4) followed by a hydroxylapatite-purification (Example 6) is applied to a wide-pore reverse-phase C4 column (Biorad RP 304). The column is eluted with a gradient of 0 to 80% acetonitrile in 0.1% trifluoroacetic acid with an increment of 0.66%/min. The flow rate is 0.5 ml/min. The fractions are collected and dried under vacuum. The residues are resuspended in 100 µl PBS containing 0.1% polyethylene glycol 6000 and tested for NAF activity. NAF elutes with a retention time of about 60 minutes, corresponding to approximately 40% acetonitrile, as a single sharp peak (FIG. 7).

Example 9

Purification of NAF by Reverse-Phase High Pressure Liquid Chromatography on a CN-propyl Column A sample of NAF purified by reversed-phase chromatography as described in Example 8, dried under vacuum and resuspended in 100 µl PBS containing 0.1% polyethylene glycol is diluted with one volume of 0.1% trifluoracetic acid and applied onto a Bakerbond wide-pore cyano(CN)-propyl column (Baker Research Products, Phillipsburg, N.J., USA). The column is eluted with a gradient extending from 0 to 50% n-propanol in 0.1% trifluoroacetic acid with an increment of 0.41%/min. The flow rate is 0.5 ml/min. Fractions are collected and dried under vacuum. The residues are resuspended in 100 µl phosphate-buffered saline containing 0.1% polyethylene glycol 6000 and tested for NAF activity. NAF elutes in two sharp peaks, a major one with a retention time of 53 min, corresponding to 22% n-propanol, and a minor one accounting for less than 30% of the total activity, with a retention time of 66 min, corresponding to 27.5% n-propanol (FIG. 8).

Example 10

Chromatofocusing of NAF

A sample of 4 ml of NAF partially purified by phosphocellulose chromatography (Example 4) is dialyzed against start buffer consisting of 25 mM ethanolamine-HCl, pH 9.4 and 0.1% polyethylene glycol 6000, and loaded onto a PBE 94 column (0.7×19 cm, Pharmacia) equilibrated with the same buffer. The column is then eluted with 200 ml of polybuffer 96-HCl (diluted 1:10 with water), pH 7.0, containing 0.1% polyethylene glycol 6000. 10-minute fractions are collected at a flow rate of 10–14 ml/h and assayed for NAF activity. Most of the activity elutes in the region of pH 8.5 to pH 8.8 (FIG. 9).

PART III

Physicochemical and Biological Characterization of NAF

Example 11

Physicochemical Properties of NAF

Partially purified NAF obtained upon phosphocellulose chromatography (Example 4) is used in these experiments.

Following phosphocellulose chromatography, fractions with the highest NAF activity are dialysed overnight at 4° against PBS using a membrane with a molecular weight cut-off of 1000 daltons. The preparation obtained is then subjected to the following treatments: a) incubation at 37° with and without trypsin, chymotrypsin or proteinase K (100 μg/ml) followed by the addition of an excess of BSA (2 mg/ml) to stop NAF proteolysis; b) heating to 56°, 80° or 95° (as compared to 22° for control); c) exposure to pH 2 or 10 (at 22°) followed by adjustment to pH 7.4 (as compared to pH 7.4 for control); d) exposure to 2 M lithium chloride, 6 M guanidinium chloride, 1% 2-mercaptoethanol or 0.5% sodium dodecyl sulfate (SDS) for 3 h at 22°, followed by dialysis for 24 h at 4° against PBS. When additions are made, samples without NAF are handled in the same way and tested for possible influence on the NAF assay.

As shown in Table 2 NAF is remarkably resistant to inactivation. Its activity is destroyed upon incubation with different proteases, indicating that NAF is a polypeptide. By contrast, NAF is not readily inactivated by heat, acid and alkaline pH conditions or by exposure to SDS. Some inactivation is obtained with 2-mercaptoethanol, lithium- and guanidinium chloride.

TABLE 2

Physicochemical properties of NAF

| Treatment | Conditions | Relative activity |
| --- | --- | --- |
| Temperature | 22°, 3 h | 100 |
|  | 56°, 1 h | 82 |
|  | 80°, 15 min | 80 |
|  | 95°, 5 min | 66 |
| pH 2.0 | 22°, 3 h | 76 |
| pH 10.0 | 22°, 3 h | 90 |
| SDS 0.5% | 22°, 3 h | 100 |
| 2-mercaptoethanol 1.0% | 22°, 3 h | 30 |
| lithium chloride 2M | 22°, 3 h | 52 |
| guanidinium chloride 6M | 22°, 3 h | 68 |
| trypsin 100 μg/ml | 37°, 4 h | 100 |
|  | 37°, 12 h | 8 |
| α-chymotrypsin 100 μg/ml | 37°, 4 h | 80 |
|  | 37°, 12 h | 1 |
| proteinase K 100 μg/ml | 37°, 12 h | 0 |

Example 12

NAF-induced Exocytosis (Induction of Granule Release by NAF in Human Neutrophils)

Neutrophils ($5 \times 10^6$/ml) suspended in PBS/BSA are preincubated with or without cytochalasin B (5 μg/ml) at 37° for 5 min.

Granule release is then initiated by adding the stimulus, e.g. NAF or a standard stimulus. The reaction is stopped 15 min later by rapid cooling in ice followed by centrifugation to sediment the cells. Vitamin B12-binding protein, β-glucuronidase and lactate dehydrogenase are determined in the cell-free media and cell pellets, and the release of these constituents is calculated in percent of the total cellular content (B. Dewalt and M. Baggiolini, *Methods Enzymol.* 132 [1986] 267).

The effects of NAF on the release of vitamin B12-binding protein and β-glucuronidase—which are constituents of the specific and the azurophil granules, respectively—are summarized in Table 3:

TABLE 3

Stimulus-dependent exocytosis of granule contents by human neutrophils

| | | Percent release of | | |
| --- | --- | --- | --- | --- |
| Stimulus | CB | Vit. B12-binding protein | β-glucuronidase | lactate dehydrogenase |
| none | − | 6.0 ± 0.4 | 2.1 ± 0.4 | 6.2 ± 2.5 |
| NAF 50 μl | − | 12.9 ± 1.6 | 2.7 ± 1.3 | 5.8 ± 0.7 |
| NAF 100 μl | − | 13.9 ± 2.1 | 3.0 ± 1.3 | 6.8 ± 2.2 |
| fMLP 0.1 μM | − | 14.0 ± 0.9 | 2.3 ± 0.8 | 5.7 ± 1.1 |
| None | + | 10.0 ± 1.1 | 2.4 ± 0.2 | 7.0 ± 3.2 |
| NAF 50 μl | + | 25.6 ± 3.4 | 7.9 ± 2.0 | 6.7 ± 1.6 |
| NAF 100 μl | + | 26.8 ± 4.9 | 8.5 ± 1.7 | 7.3 ± 2.1 |
| fMLP 0.1 μM | + | 35.6 ± 5.5 | 12.1 ± 4.4 | 5.3 ± 1.6 | mean values ± SD

In normal neutrophils NAF induces exocytosis of specific granules only. When the cells are pretreated with cytochalasin B, however, extensive release from both types of granules is obtained. Under the latter conditions, the release of β-glucuronidase is paralleled by that of elastase, the marker used to test for NAF activity (Example 1). In quantitative terms, the exocytosis-inducing properties of NAF are similar to those of the chemotactic peptide fMLP. Neither stimulus induces the release of the cytosolic enzyme lactate dehydrogenase, indicating that cell damage is negligible.

Example 13

NAF-Induced Respiratory Burst (Induction of Superoxide Formation by NAF in Human Neutrophils)

Superoxide formation is measured at 37° as the SOD sensitive reduction of ferricytochrome c (M. Markert et al., *Methods Enzymol.* 132 [1984] 267). The assay mixture (800 μl) consists of $0.75 \times 10^6$ cells/ml PBS-BSA containing 85 μM cytochrome c. Absorbance changes are recorded in a Hewlett-Packard 8451A diode array spectrophotometer equipped with a thermostated seven-place cuvette exchanger. Table 4 documents the capacity of NAF to elicit the respiratory burst in human neutrophils:

TABLE 4

NAF-dependent superoxide production by human neutrophils

| | Cytochrome c reduction+ | |
| --- | --- | --- |
| NAF (μl) | Maximum rate (nmol/min) | Total in 3 min (nmol) |
| 5 | 0.81 | 0.89 |
| 10 | 1.45 ± 0.63 | 1.45 ± 0.50 |
| 20 | 2.32 ± 0.56 | 2.16 ± 0.39 |
| 30 | 2.51 ± 0.50 | 2.30 ± 0.55 |
| 50 | 3.51 ± 0.69 | 3.10 ± 0.55 |
| 100 | 3.69 | 3.39 |

+all values are expressed per $10^6$ cells
mean values ± SD

A gradual increase in maximum rate and total amount of superoxide generation is obtained with increasing amounts of NAF. As can be shown by comparative experiments, the amounts of NAF eliciting maximum levels of superoxide production correspond to those inducing maximal exocytosis.

Example 14

H$_2$O$_2$ formation (comparison of NAF with fMLP and C5a as Stimulus of the Respiratory Burst in Human Neutrophils)

The properties of NAF, fMLP and C5a as stimuli of the respiratory burst are compared by assessing the production of superoxide or hydrogen peroxide by the stimulated cells. Superoxide formation is determined as described in Example 13. Hydrogen peroxide formation is determined by chemiluminescence (M. P. Wymann et al., *Anal. Biochem.* 165 [1987] 371–378). The assay mixture consisting of PBS-BSA containing 0.1 M sodium azide, 0.01 mM luminol, 9 U/ml horseradish peroxidase and 10$^6$ neutrophils is preincubated for 10 min at 37° and the reaction is started by adding the stimulus via a microsyringe.

FIG. 10 shows superoxide formation induced by increasing amounts of NAF. Owing to its rapid onset, high rate and early levelling-off, the response to NAF resembles closely that elicited by fMLP or C5a. The response to NAF is markedly enhanced by pretreatment of the cells with PAF (FIG. 10), which also enhances superoxide production induced by fMLP or C5a. A direct comparison of the responses to NAF, fMLP and C5a is shown in FIG. 9. The chemiluminescence recordings of the rate of H$_2$O$_2$ formation versus time underlines the similarity of the responses. These as well as other measurements show in addition that the time between stimulus addition and onset of H$_2$O$_2$ production induced by NAF, fMLP and C5a are identical and amount to about 2 sec, as previously reported for fMLP, C5a, PAF and leukotriene B$_4$ (M. P. Wymann et al., *J. Biol. Chem.* 262 [1987] 12048). The qualitative and quantitative similarity of the neutrophil response to NAF, fMLP and C5a indicates that NAF activates neutrophils by binding to a surface receptor and thus behaves like a receptor agonist.

Example 15

Discrimination Between NAF and C5a

As reported in Example 14, the profile of NAF activity towards human neutrophils is similar to that of C5a. The similarities between these two peptides extend to distinguishing physicochemical properties like the resistance to heat and acid.

Since C5a and NAF have similar effects on neutrophils, further experiments must be performed to discriminate entirely between the two. Samples of NAF and C5a are exposed to fresh human serum. This treatment is known to convert C5a to its relatively inactive des-arginyl derivative by cleavage through a carboxypeptidase. As shown in FIG. 11 serum treatment completely abolishes the activity of C5a but does not affect that of NAF. This shows that these two agents are structurally different.

Example 16

Evidence that NAF has its Own Specific Receptor on Neutrophils

When neutrophils are stimulated twice with the same amount of the same receptor agonist (e.g. fMLP) and superoxide production is recorded as a measure of the neutrophil response, the second stimulation is virtually inactive. On the other hand, when agonists acting on different receptors are used in sequence.(e.g. fMLP followed by C5a) these stimulations yield a normal response. Experiments of this type are therefore used to find out whether NAF acts by its own receptor or via a receptor also used by other agonists.

FIG. 12*a* shows that neutrophils respond normally to fMLP following a first challenge with NAF or C5a. In FIG. 12*b* the results of repeated stimulation with NAF and C5a are shown. The cells are stimulated first with NAF and C5a at concentrations that elicit about the same amount of superoxide formation and then a second time with either the same or the alternate stimulus. When the same agonist is applied twice the cells do not respond to the second stimulation. By contrast, a normal response is obtained to C5a in cells challenged first with NAF, and to NAF in cells challenged first with C5a. Since the neutrophils show complete desensitization to either stimulus but no cross-desensitization, NAF and C5a appear to exert their stimulatory effects via unrelated receptors, indicating that they are structurally different. Combinations of NAF with PAF, fMLP and leukotriene B$_4$ also fail to show cross-desensitization. NAF therefore acts through a selective, hitherto unknown receptor.

Example 17

Neutrophil Accumulation and Plasma Leakage Induced by NAF in the Rabbit

Inflammatory responses are examined in the skin of conscious 2.0 to 2.5 kg New Zealand albino rabbits. Erythrocytes in blood from donor rabbits are sedimented with hydroxyethyl cellulose (Polysciences, Warrington, Pa.) and neutrophils in the resultant leucocyte-rich plasma are purified (>94% neutrophils) by density gradient centrifugation on Percoll (Pharmacia, Uppsala, Sweden). Cells are resuspended in Ca$^{2+}$ and Mg$^{2+}$—free Tyrode's solution containing 10% platelet poor plasma to a concentration of 10$^6$ leukocytes/ml and labeled for 15 min at room temperature with 40 µCi $^{111}$indium-oxine (Amersham) per 10$^6$ cells. The labeled cells are washed by centrifugation through 10% platelet-poor plasma and approximately 10$^6$ cells per recipient are mixed with 10 µCi $^{125}$iodine-labeled human serum albumin (Amersham) and injected intravenously through the lateral ear vein of rabbits with inflammatory lesions under study. Intradermal injections of inflammatory agents are then made and animals are killed 2 h later in studies with actinomycin D and polymyxin B, and 4 h later in dose-response experiments. Midway through the period that radiolabeled cells are in circulation, a blood sample is collected and the specific activities of neutrophils and plasma in blood are determined. Radioactivity in inflammatory lesions at the end of each experiment are determined in a multichannel gamma counter, the activity in control skin sites is subtracted and the absolute number of neutrophils and volume of plasma accumulating in inflammatory lesions are calculated from the specific activities. Neutrophil numbers in inflammatory lesions are standardised between animals by expressing the results as cell number per 10$^6$ neutrophils circulating per ml peripheral blood, according to the method of Cybulsky et al., *Am. J. Pathol.* 124 [1986] 367.

Recombinant NAF obtained as described under Example 19 is dissolved at 400 µg/ml in minimal essential medium (50 mM) plus 0.45 M NaCl (pH 6.5). Endotoxin (*E. coli* serotype 055:B5, Sigma, St. Louis, Mo.) is dissolved in pyrogen-free normal saline. fMLP is dissolved in dimethyl sulphoxide at 10$^{-2}$ M and diluted to working concentrations in PFS. Polymyxin B and actinomycin D are dissolved in 1 ml ethanol and diluted 20 fold by mixing with NAF, endotoxin or fMLP in PFS. In studies on inhibition of inflammatory responses 40 µg polymyxin B and 10$^{-7}$ moles actinomycin D are injected per skin site with 10$^{-6}$ moles endotoxin. In all experiments 0.2 ml of inflammatory agents are injected intradermally per site through 26 gauge needles, with 5 replicates of each treatment in each animal.

NAF induces a dose-dependent increase in plasma leakage (FIG. 16) and neutrophil accumulation (FIG. 17) over the dose range tested ($10^{-11}$ to $10^{-9}$ moles per site). In comparison endotoxin causes plasma leakage (FIG. 16) and neutrophil accumulation (FIG. 17) of comparable intensity at $10^{-13}$ moles per site. In five rabbits NAF is 3 to 10 times more potent than fMLP as a stimulus for plasma leakage and neutrophil accumulation. Neutrophil accumulation induced by dilution of the buffer used to dissolve NAF to the concentration present in solutions delivering $10^{-9}$ moles per site does not differ from responses in sites receiving PFS alone. The possibility that the activity of the NAF preparation may be due to an endotoxin contaminant is examined by injecting polymyxin B (40 µg/site) together with NAF, fMLP or endotoxin. Polymyxin B causes 84% inhibition of the response to endotoxin ($10^{-13}$ moles) but is without effect on neutrophil accumulation induced by NAF ($10^{-9}$ moles) or fMLP ($10^{-9}$ moles) (FIG. 18).

Injection of a non-reversible inhibitor of RNA transcription, actinomycin D ($10^{-7}$ moles/site) together with $10^{-13}$ moles endotoxin causes 90% inhibition of neutrophil accumulation (FIG. 19). In contrast actinomycin D has no effect on neutrophil accumulation induced by NAF ($10^{-9}$ moles) or fMLP ($10^{-9}$ moles) (FIG. 19).

The results show that NAF is active in vivo and induces dose-dependent accumulation of neutrophils and leakage of plasma into inflammatory lesions. The molar potency of NAF is comparable to the classical chemotactice C5a and LTB and 3 to 5 fold higher than fMLP. Neutrophil accumulation induced by NAF is not inhibited by the concomitant intradermal injection of a protein synthesis inhibitor (actinomycin D). NAF thus acts directly, like a chemotactic agonist such as fMLP and unlike endotoxin.

Example 18

NAF-Induced Exocytosis (Effect on rabbit Neutrophils)

Rabbit neutrophils are isolated from peripheral blood (obtained from the ear vein or artery) by dextran sedimentation followed by Hypaque-Ficoll density gradient centrifugation. Purified natural NAF is used.

Exocytosis conditions: $0.6 \times 10^6$ cells (in a total volume of 0.15 ml) pretreated with cytochalasin B for 5 min at 37° are stimulated with NAF (0.1–100 nM) or fMLP (100 nM) for 15 min. N-acetyl-β-glucosaminidase, an azurophil granule marker, is determined in the cell-free medium. The results are shown in Table 5:

TABLE 5

NAF-induced exocytosis

| Stimulus | Concentration (nM) | N-acetyl-β-glucosaminidase (pmol/min) |
| --- | --- | --- |
| none |  | 41 |
| NAF | 0.1 | 53 |
|  | 1.0 | 99 |
|  | 10.0 | 139 |
|  | 100.0 | 157 |
| fMLP | 100.0 | 181 |

PART IV

Recombinant NAF

Example 19

Synthesis and Expression of NAF in E.coli a) Oligonucleotide Synthesis and Purification The oligonucleotides ON-1 to ON-6 (see FIG. 13) are synthesized on an automated DNA synthesizer using standard chemistry with 3'-β-cyanoethyl-N,N-diisopropylphosphoamidite nucleosides as monomers, on a solid support such as Fractosil silica gel or controlled porous glass (CPG) (S. L. Beaucage and M. H. Caruthers, Tetr. Letters 22 [1981] 1859; N. D. Sinha et al., Nucleic Acids Res. 12 [1984] 4539).

The detritylated materials are separated from the support by a 2-hour treatment with 25% ammonia at room temperature, all protecting groups are split off by heating the ammoniacal solution for 20 hours to 55° and the products lyophilized. Separation of the raw materials is effected by polyacrylamide-gel electrophoresis (PAGE) with 12% acrylamide, 0.3% bisacrylamide, 7 M urea, 0.089 M tris-borate, 0.089 M boric acid, 0.002 M EDTA at 20 V/cm. Full-length oligonucleotides are located by UV-shadowing on fluorescence silica gel plates, the gel portions are cut out and electroeluted in an elution chamber. The concentrated solutions are desalted on a Biogel P2 column (30×0.9 cm) by elution with 10% ethanol and lyophilized. Samples of ON-1 to ON-6 are radioactively labelled with $^{32}$P-γ-ATP and polynucleotide kinase. Analysis by PAGE and autoradiography confirms that they are homogeneous. Correct sequences are confirmed by Maxam-Gilbert sequencing of the oligonucleotides immobilized on a modified filter paper (A. Rosenthal et al., Nucleic Acids Res. 13 [1985] 1173–1184).

b) Annealing and Ligation

For annealing and ligation, 250 pmol portions of the oligonucleotides are phosphorylated with 4 µCi $^{32}$P-ATP (5000 µCi/mmol) and 9 units of polynucleotide kinase in 20 µl kinase buffer (T. Maniatis et al., Molecular Cloning, A Laboratory Manual [1982], Cold Spring Harbor Laboratory, N.Y.) for 40 min at 37°, followed by a 20-min chase with 5 mmol unlabeled ATP. The reaction is stopped with 1 µl 0.5 M EDTA at 70°. The phosphorylated oligonucleotides are purified by adsorption on NENSORB 20 cartridges (Du Pont) and elution with 20% ethanol and the yield is approximately 90%. Simultaneous annealing and ligation of equal amounts of 30 to 100 pmol of 5'-phosphorylated ON-2 to ON-5 and unphosphorylated ON-1 and ON-6 is done in 25 µl buffer (125 mM Tris-HCl, pH 7.6) containing 25 mM MgCl$_2$. The mixture is heated to 90° for 4 min, cooled to 14° within 3 h and incubated for a further 14 h at 14°. The volume is adjusted to 60 µl with 50 nM Tris-HCl, pH 7.6, 10 mM MgCl$_2$, 10 mM dithiothreitol, 1 mM ATP, 0.1 mg/ml bovine serum albumin containing 1600 to 2000 units T4-ligase. Ligation is performed for 14 h at 14° and stopped by addition of 1 µl 0.5 M EDTA and heating to 70°. After phenol extraction the aqueous solution is brought to 0.3 M sodium acetate, 0.01 M magnesium acetate, the DNA is precipitated with ethanol and the products purified by PAGE (8% acrylamide, 7 M urea) with a maximum loading of 10 pmol DNA per 1.5 cm slot of a 0.5 mm thick gel. The product of correct length is identified by autoradiography, the gel segment excised and the DNA is electroeluted for 6 h at 200 V in Biotrap BT100 and ethanol precipitated, giving a final yield of 5 to 8 pmol of purified double-stranded DNA per 100 pmol oligonucleotide.

c) Cloning of Synthetic Gene

A sample of 110 ng of the isolated synthetic NAF gene is ligated with 260 ng of agarose gel-purified SphI/BamHI-cut pBS M13⁻ plasmid DNA (Stratagene). One-tenth of this ligation mixture is used to transform 200 μl *E.coli* strain 5K cells made competent by the method of D. Hanahan, *J. Mol. Biol.* 166 [1983] 557–580, and approximately 320 ampicillin-resistant colonies are produced per ng of input DNA. Six clones are picked and grown overnight in L-Broth/ampicillin. Plasmid DNA is prepared (H. C. Birnbolm and J. Doly, *Nucleic Acids Res.* 7 [1979] 1513–71523) and run on a 1% agarose gel. Pure supercoiled DNA is isolated by electrophoresing the bands into 3MM paper (Whatman) and centrifuging into Eppendorf tubes. After phenol extraction and ethanol precipitation, the DNA is sequenced by the alkali-denatured plasmid chain termination method using T3 and T7 primers (Stratagene) and the sequenase enzyme (E. J. Chen et al., *DNA* 4 [1985] 165–170).

Of the 6 clones three, i.e. clones 1, 2 and 6, contained the correct NAF sequence. The other three clones had mistakes: clone 3 had an extra G residue inserted after the ATG starting codon, whereby the full coding sequence is put out of phase. In clone 5, C is replaced by T in position 34, whereby a stop codon is formed after amino acid No. 6. Finally, clone 4 is lacking a G in position 13. This position is not in the coding sequence but in the region between the start codon and the ribosome binding site.

The plasmid containing the correct sequence (clone 6) is cut with restriction enzymes ClaI and BamHI and the 237 bp fragment isolated from an agarose gel by elution into 3 MM paper as above. This fragment is then ligated to a linear DNA fragment containing, from left to right:

- a BamHI restriction endonuclease site;
- a synthetic transcription terminator (CCCGGGCGATGAATCGCCCGGG or CCCGGGCGATTCATCGCCCGGG);
- a section of plasmid pAT153, from the SalI site at nucleotide no. 651 through the origin of replication and the ampicillin-resistance gene to the EcoRI site at nucleotide no. 0;
- the *E. coli* tryptophan promoter;
- a ClaI site situated approximately 5 base pairs downstream of the ribosome binding site in the promoter.

The resulting ampicillin-resistant expression plasmid, designated p(NAF)-6T3 (FIG. 14) is transformed into *E. coli* cells of strain HB101.

The transcription terminator is not essential for the expression of NAF in *E. coli*. It allows efficient termination of the NAF-mRNA produced by the *E. coli* polymerase and thus increases the yield in expression. NAF can however also be expressed in the same vector without the transcription terminator, but the yield is then, however, 30 to 50% lower.

This synthetic gene coding for NAF as well as other genes coding for the same basic peptide sequence but having a different nucleotide sequence or coding for peptides of varying lengths may also be expressed in *E. coli* using other promoters, e.g. the lambda PL or the *E. coli* Lac or Tac promoters. The genes may also be introduced using other vectors and expressed in other organisms, e.g. in yeasts, fungi, animal cells, bacterial cell lines, plants and transgenic higher organisms.

c) Expression

Expression of p(NAF)-6T3 in *E. coli* HB 101 is effected as follows:

Preculture 1: 50 μl of a glycerol culture of the cell line kept at −20° are added to 10 ml of sterile LB medium (10 g/l tryptone, 5 g/l yeast extract, 10 g/l NaCl) containing 100 μg/ml ampicillin. The culture is shaken in an incubator for 8 hours at 37° and 200 rpm.

Preculture 2: 8 ml from preculture 1 medium are inoculated into 1 l of M9 medium (J. H. Miller *Experiments in Molecular Genetics* [1972] Cold Spring Harbor Laboratory, N.Y., p. 431–433) containing 0.2% glucose, 0.5% casamino acids (Difco), 25 mg/l tryptophane and 100 μg/ml ampicillin. This culture is shaken in an incubator for 15–16 hours at 370 and 200 rpm.

Fermentation: the main fermentation is effected in a 70 l fermentor at a working volume of 35 l. The same medium is used as for preculture 2 with the exception that only 5 mg/l tryptophane are added. Preculture 2 is inoculated into this medium and fermentation is continued at 37° up to an optical density of 2.8 at 600 nm ($OD_{600}$). When $OD_{600}$ reaches 2.8, indole-acrylic acid in ethanol is added to a final concentration of 20 mg/l. After 4 hours the $OD_{600}$ has increased to 13.5; centrifugation yields a 516 g pellet.

d) Purification of Recombinant NAF

*E. coli* cells containing recombinant NAF are stored at −20°. Batches of 100 g are washed with 100 ml 20 mM Tris-HCl, pH 8.0, containing 50 mM NaCl, resuspended in 250 ml of the same buffer and disrupted at 2500 psi in a French Press (Aminco). After centrifugation at 47000 g for 40 min the pellet is resuspended in the same buffer, recentrifuged and stored at −20°. Portions of 10 g are suspended in 100 ml 50 mM MES-NaOH, pH 6.5, 6M guanidine-HCl, stirred for 1 h and dialyzed against 0.5% acetic acid. The dialysate is clarified by centrifugation and loaded in aliquots on a Mono-S column (HR 5/5, Pharmacia). The column is washed with 50 mM MES-NaOH, pH 6.5, containing 0.2 M NaCl and eluted at a rate of 0.5 ml/min with a linear gradient in the same buffer (0.2 to 0.5 M NaCl). The fractions with the highest NAF content are pooled and chromatographed on a wide-pore reverse-phase HPLC column (0.46×125 mm Vydac C4TP) in 0.1% trifluoroacetic acid and a 20 to 60% acetonitrile gradient at a flow rate of 1 ml/min.

PART V

Identity of Natural and Recombinant NAF

Example 20

Physicochemical Identity

The NAF recovered from HPLC (see Example 19) is considered pure on the basis of two criteria: silver-stained SDS-polyacrylamide gels show a single band coinciding with natural NAF (1 μg recombinant NAF from HPLC peak fraction in Lane 2 vs 1 μg natural NAF in Lane 3, with molecular weight standards cytochrome c [12.5 kd] and aprotinin [6.5 kd] in Lane 1), and Edman degradation of the formic acid—cleaved peptide yields amino- and carboxy-terminal sequences corresponding to those of the 72-amino acid natural NAF. Amino acid analysis is in accord with the composition expected from the sequence. No methionine is found indicating that this residue is probably removed by the bacteria.

Example 21

Biochemical Identity

Natural and recombinant NAF are tested in parallel on human neutrophils. They elicit virtually identical changes in cytosolic free $Ca^2+$, yielding a maximum rise at a concentration as low as 3 nM (FIG. 15). A nearly identical concentration-dependent respiratory burst response is obtained with both preparations in the range of 1 to 30 nM as assessed by chemiluminescence. The equivalence between natural and recombinant NAF is also reflected by chemotaxis and exocytosis measurements. Chemotactic migration is observed between 0.1 and 10 nM with a maximum effect at 1 nM. (Table 6). With either peptide a significant release of vitamin $B_{12}$-binding protein from the specific granules at 0.3 nM and of beta-glucuronidase from the azurophil granules at 1 nM is observed. This effect increases with the stimulus concentration as shown in Table 7:

TABLE 6

NAF-induced neutrophil chemotaxis

| NAF (nM) | nat | rec |
|---|---|---|
| 0.1 | 98 ± 6 | 88 ± 6 |
| 1.0 | 123 ± 6 | 124 ± 3 |
| 10.0 | 127 ± 3 | 126 ± 4 |

Values represent means ± SD of leading front migration in μm (n = 3).
Random migration in absence of a chemotactic stimulus is 61 ± 5 μm.
nat = natural NAF
rec = recombinant NAF

TABLE 7

NAF-induced exocytosis

| NAF (nM) | Vit. $B_{12}$ binding protein | | beta-glucuronidase | |
|---|---|---|---|---|
| | nat | rec | nat | rec |
| 0.3 | 7.8 ± 3.6 | 5.4 ± 2.0 | 1.1 ± 0.8 | 0.8 ± 0.6 |
| 3.0 | 21.9 ± 4.2 | 20.2 ± 3.7 | 8.2 ± 1.9 | 7.1 ± 1.7 |
| 30.0 | 28.4 ± 3.7 | 28.1 ± 3.8 | 14.2 ± 2.1 | 12.9 ± 2.9 |

Percent release from cytochalasin B pretreated neutrophils (4 × 10⁶ cells/ml) stimulated for 10 min with natural (nat) or recombinant (rec) NAF. Release from the corresponding unstimulated controls is deducted. Means ± SD (n = 3).

3700/VA

What is claimed is:

1. A peptide whose complete amino acid sequence is
X-Leu-Arg-Cys-Gln-Cys-Ile-Lys-Thr-Tyr-Ser-Lys-Pro-Phe-His-Pro-Lys-Phe-Ile-Lys-Glu-Leu-Arg-Val-Ile-Glu-Ser-Gly-Pro-His-Cys-Ala-Asn-Thr-Glu-Ile-Ile-Val-Lys-Leu-Ser-Asp-Gly-Arg-Glu-Leu-Cys-Leu-Asp-Pro-Lys-Glu-Asn-Trp-Val-Gln-Arg-Val-Val-Glu-Lys-Phe-Leu-Lys-Arg-Ala-Glu-Asn-Ser,
 wherein X is Ala-Val-Leu-Pro-Arg-Ser-Ala-Lys-Glu-, Lys-Glu- or Glu-,
said peptide activating human neutrophil leukocytes and being in isolated and substantially pure form.

2. A peptide according to claim 1 wherein X is Ala-Val-Leu-Pro-Arg-Ser-Ala-Lys-Glu-.

3. The peptide according to claim 2 wherein the cysteine residues in positions 12 and 39 are linked by a disulfide bond and the cysteine residues in positions 14 and 55 are linked by a disulfide bond.

4. A peptide according to claim 1 wherein X is Lys-Glu-.

5. The peptide according to claim 4 wherein the cysteine residues in positions 5 and 32 are linked by a disulfide bond and the cysteine residues in positions 7 and 48 are linked by a disulfide bond.

6. A peptide according to claim 1 wherein X is Glu-.

7. The peptide according to claim 6 wherein the cysteine residues in positions 4 and 31 are linked by a disulfide bond and the cysteine residues in positions 6 and 47 are linked by a disulfide bond.

8. A pharmaceutical composition comprising a peptide whose complete amino acid sequence is
X-Leu-Arg-Cys-Gln-Cys-Ile-Lys-Thr-Tyr-Ser-Lys-Pro-Phe-His-Pro-Lys-Phe-Ile-Lys-Glu-Leu-Arg-Val-Ile-Glu-Ser-Gly-Pro-His-Cys-Ala-Asn-Thr-Glu-Ile-Ile-Val-Lys-Leu-Ser-Asp-Gly-Arg-Glu-Leu-Cys-Leu-Asp-Pro-Lys-Glu-Asn-Trp-Val-Gln-Arg-Val-Val-Glu-Lys-Phe-Leu-Lys-Arg-Ala-Glu-Asn-Ser,
 wherein X is Ala-Val-Leu-Pro-Arg-Ser-Ala-Lys-Glu-, Lys-Glu- or Glu-,
said peptide activating human neutrophil leukocytes, and a pharmaceutically acceptable carrier or diluent.

9. A method of treating a condition accompanied or caused by a modification of the number or activation state of polymorphonuclear cells-neutrophils comprising administering to a host in need of such treatment an effective amount of a peptide whose complete amino acid sequence is
X-Leu-Arg-Cys-Gln-Cys-Ile-Lys-Thr-Tyr-Ser-Lys-Pro-Phe-His-Pro-Lys-Phe-Ile-Lys-Glu-Leu-Arg-Val-Ile-Glu-Ser-Gly-Pro-His-Cys-Ala-Asn-Thr-Glu-Ile-Ile-Val-Lys-Leu-Ser-Asp-Gly-Arg-Glu-Leu-Cys-Leu-Asp-Pro-Lys-Glu-Asn-Trp-Val-Gln-Arg-Val-Val-Glu-Lys-Phe-Leu-Lys-Arg-Ala-Glu-Asn-Ser,
 wherein X is Ala-Val-Leu-Pro-Arg-Ser-Ala-Lys-Glu-, Lys-Glu- or Glu-,
said peptide activating human neutrophil leukocytes.

10. A method according to claim 9 wherein the condition is a bacterial, mycoplasma, yeast, fungal or viral infection.

11. A method according to claim 9 wherein the condition is an inflammation.

12. A method of increasing the number or raising the activation state of polymorphonuclear cells-neutrophils in a host comprising administering to a host in need of a greater number or higher activation state of polymorphonuclear cells-neutrophils a therapeutically effective amount of a peptide whose complete amino acid sequence is
X-Leu-Arg-Cys-Gln-Cys-Ile-Lys-Thr-Tyr-Ser-Lys-Pro-Phe-His-Pro-Lys-Phe-Ile-Lys-Glu-Leu-Arg-Val-Ile-Glu-Ser-Gly-Pro-His-Cys-Ala-Asn-Thr-Glu-Ile-Ile-Val-Lys-Leu-Ser-Asp-Gly-Arg-Glu-Leu-Cys-Leu-Asp-Pro-Lys-Glu-Asn-Trp-Val-Gln-Arg-Val-Val-Glu-Lys-Phe-Leu-Lys-Arg-Ala-Glu-Asn-Ser,
 wherein X is Ala-Val-Leu-Pro-Arg-Ser-Ala-Lys-Glu-, Lys-Glu- or Glu-,
said peptide activating human neutrophil leukocytes.

\* \* \* \* \*